(12) United States Patent
Uchikubo

(10) Patent No.: US 6,602,185 B1
(45) Date of Patent: Aug. 5, 2003

(54) REMOTE SURGERY SUPPORT SYSTEM

(75) Inventor: Akinobu Uchikubo, Oume (JP)

(73) Assignee: Olympus Optical Co., Ltd. (JP)

( * ) Notice: Subject to any disclaimer, the term of this patent is extended or adjusted under 35 U.S.C. 154(b) by 0 days.

(21) Appl. No.: 09/503,520

(22) Filed: Feb. 14, 2000

(30) Foreign Application Priority Data

| Feb. 18, 1999 | (JP) | ......... H11-040362 |
| Feb. 26, 1999 | (JP) | ......... H11-051556 |
| Mar. 15, 1999 | (JP) | ......... H11-068609 |
| Mar. 25, 1999 | (JP) | ......... H11-082198 |
| May 9, 1999 | (JP) | ......... H11-102991 |

(51) Int. Cl.[7] .................. A61B 1/00
(52) U.S. Cl. ............ 600/118; 606/1; 606/130
(58) Field of Search .......... 600/103, 117, 600/118; 606/130, 1

(56) References Cited

U.S. PATENT DOCUMENTS

| 5,678,568 A | | 10/1997 | Uchikubo et al. ......... 128/897 |
| 5,762,458 A | * | 6/1998 | Wang et al. ............... 414/1 |
| 5,808,665 A | * | 9/1998 | Green ..................... 348/65 |
| 6,006,191 A | * | 12/1999 | DiRienzo .................. 705/2 |
| 6,132,368 A | * | 10/2000 | Cooper .................... 600/102 |
| 6,139,542 A | * | 10/2000 | Hohla ..................... 606/10 |
| 6,223,100 B1 | * | 4/2001 | Green ..................... 600/109 |

* cited by examiner

Primary Examiner—John Mulcahy
(74) Attorney, Agent, or Firm—Ostrolenk, Faber, Gerb & Soffen, LLP

(57) ABSTRACT

A first signal transmission apparatus installed in an operating room and a second signal transmission apparatus installed in a remote control room in a remote place are linked by a public line. Assuming that surgery is performed on a patient using a surgical instrument in the operating room while endoscopic images are viewed, the surgical instrument can be controlled using a first controller. The control and patient data are displayed on a display device via a second controller connected to the second signal transmission apparatus. The state of the surgical instrument and the patient data can always be checked in the remote control room. Surgical instructions or any other surgical support can be given easily.

21 Claims, 22 Drawing Sheets

REMOTE SURGERY SUPPORT SYSTEM

BACKGROUND OF THE INVENTION

1. Field of the Invention

The present invention relates to a remote surgery support system for remotely supporting surgery.

2. Description of the Related Art

Normally, an operator performs surgery on a patient in an operating room. For example, an operator in an operating room may have to carry out a surgical procedure in which the operator has little experience. A support system for helping the operator appropriately perform surgery on a patient in an operating room is presumably such that the operator in the operating room can perform surgery while remotely supported by a remotely supporting operator. Specifically, the operator in the operating room communicates with the remotely supporting operator staying in a remote place over a public line, and receives instructions on a region to be resected from the remotely supporting operator during surgery.

Related arts concerning the remote surgery support system for remotely supporting surgery include an art disclosed in Japanese Patent Application No. 10-318019.

According to the related art, when surgery is performed by controlling the movement of a surgical instrument using a manipulator, an operator in an operating room is informed the contents of a manipulation expressed by a manipulation signal produced when a remotely supporting operator controls the surgical instrument. Consequently, the operator in the operating room can smoothly carry out a surgical procedure with the help of the remotely supporting operator.

However, according to the related art, the remotely supporting operator cannot monitor the state of the surgical instrument in the operating room. For instructing the way of manipulating the surgical instrument from a remote control room to the operating room, the remotely supporting operator must ask verbally the state of the surgical instrument from time to time. A surgical procedure is therefore suspended frequently. Consequently, there is an increasing demand for an environment in which surgery can be performed more smoothly.

Moreover, the remotely supporting operator has no means for checking patient data. Patient information must therefore be sent to the remotely supporting operator. In case of emergency surgery, it is impossible to make patient information timely available in a remote place.

SUMMARY OF THE INVENTION

An object of the present invention is to provide a remote surgery support system making it possible to readily check the state of a surgical instrument and/of patient information in a remote place over a communication line.

Another object of the present invention is to provide a remote surgery support system making it possible to give instructions on surgery while readily checking the state of a surgical instrument and/or patient information in a remote place over a communication line.

Still another object of the present invention is to provide a surgical information display method making it possible to observe endoscopic images and readily check the state of a surgical instrument and/or patient information.

A remote surgery support system consists mainly of:
a first control means installed in an operating room for controlling a surgical instrument;
an input means for use in inputting control information, with which the surgical instrument is controlled, to the first control means;
a first signal transmission apparatus for receiving information, which indicates the controlled state of the surgical instrument, from the first control means, and converting the information into a transmissible signal;
a communication line over which the transmissible signal converted by the first signal transmission apparatus to a control room in a remote place;
a second signal transmission apparatus for receiving the transmissible signal from the first signal transmission apparatus over the communication line, and converting the signal into a signal corresponding to the information;
a second control means for receiving the signal from the second signal transmission apparatus; and
a display device for visualizing an output of the second control means.

Consequently, an operator staying in the remote place can monitor the state of the surgical instrument.

The remote surgery support system further includes:
a second input means for supplying support information to the second control means; and
a second display device for inputting the support information from the second control means via the second signal transmission apparatus and the first signal transmission apparatus, and displaying the information.

Consequently, the operator in the remote place can input support information concerning a procedure at the second input means to the second control means. The input support information is displayed on the second display device via the second signal transmission apparatus and the first signal transmission apparatus. The operator in the operating room can carry out the procedure.

BRIEF DESCRIPTION OF THE DRAWINGS

FIG. 1 schematically shows the overall configuration of a remote surgery support system in accordance with the first embodiment;

FIG. 2 is a block diagram showing the detailed configuration of the remote surgery support system shown in FIG. 1;

FIG. 3 is a block diagram showing the configuration of a controller in a surgery system;

FIG. 4 is a block diagram showing the configuration of a second controller in a remote support system;

FIG. 5 shows the contents of display on a display screen of a display device;

FIG. 6 is a flowchart describing a sequence of information display involving the surgery system and remote support system;

FIG. 9 schematically shows the overall configuration of a remote surgery support system in accordance with the fourth embodiment;

FIG. 10 is a block diagram showing the detailed configuration of the remote surgery support system shown in FIG. 9;

FIG. 14 is an explanatory diagram showing the overall configuration of a medical information processing system;

FIG. 15 is a block diagram showing the configuration of an information accumulation system;

FIG. 16 is a block diagram showing the functional configuration of a control circuit;

FIG. 17 is an explanatory diagram showing an example of a medical information display screen;

FIG. 18 is an explanatory diagram showing an example of a clinical recording printout;

FIG. 19 is an explanatory diagram showing the overall configuration of a medical information processing system;

FIG. 20 is a block diagram showing the configuration of a control apparatus for producing clinical recordings;

FIG. 21 is an explanatory diagram showing an example of a displayed integrated information screen; and FIG. 22 is an explanatory diagram showing an example of the contents of a printed clinical recording.

DESCRIPTION OF PREFERRED EMBODIMENTS

Figure 1:
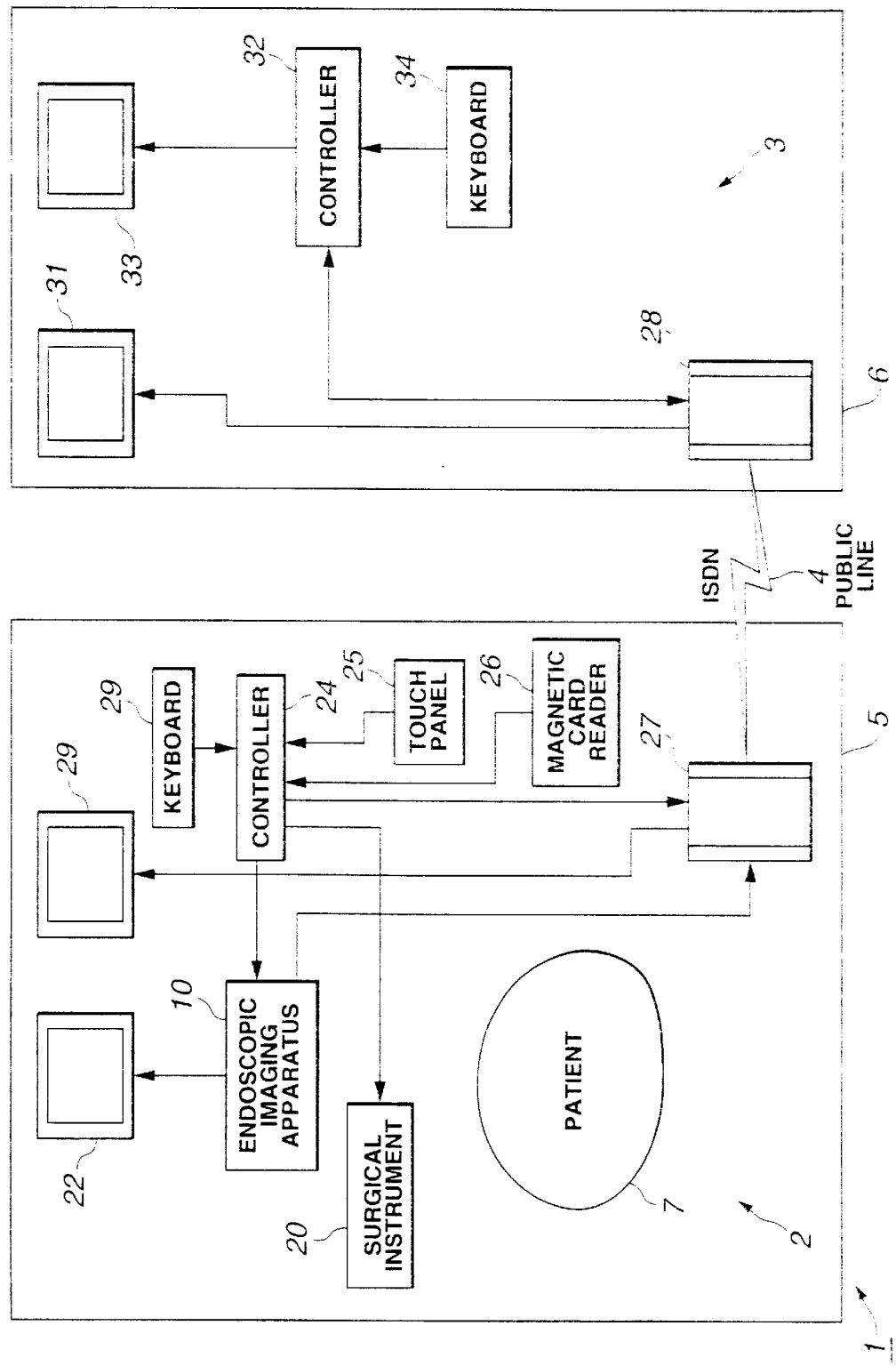
FIG. 1 to FIG. 6 relate to the first embodiment of the present invention.

Referring to the drawings, embodiments of the present invention will be sequentially described below. To begin with, the first embodiment will be described with reference to FIG. 1 to FIG. 6.

The present embodiment is a remote surgery support system in which: an operating room and a remote control room in a remote place are liked with a communication line; and an operator in the operating room receives support information from the remote control room and performs surgery.

Figure 2:
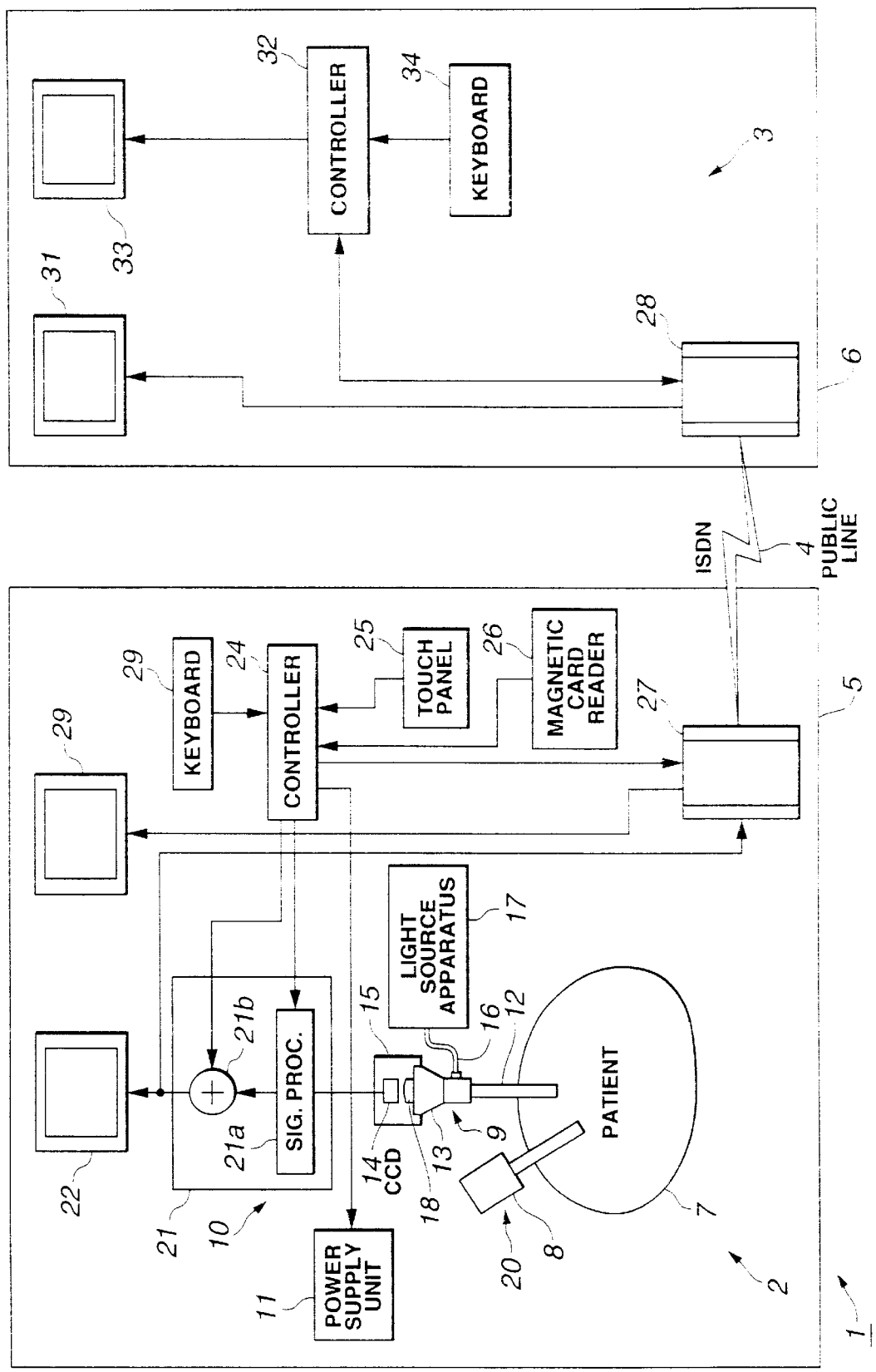

As shown in FIG. 1 or FIG. 2, a remote surgery support system 1 in accordance with the first embodiment of the present invention has a surgery system 2 connected to a remote support system 3, which is installed remotely to the surgery system 2, over a public line 4. The surgery system 2 and remote support system 3 are installed in an operating room 5 and a remote control room (remote support system room) 6 respectively.

The surgery system 2 installed in the operating room 5 has an endoscopic imaging apparatus 10 and a surgical apparatus (surgical instrument) 20. The endoscopic imaging apparatus 10 is used to observe an intracavitary region of a patient 7, and the surgical apparatus (surgical instrument) 20 is used to perform surgery on the patient 7 for curing a lesion under observation through the endoscopic imaging apparatus 10.

To be more specific, as shown in FIG. 2, a surgical instrument body 8 and an optical endoscope 9 are thrust into, for example, the abdominal cavity of the patient 7. The surgical instrument body 8 is used to perform surgery for curing a lesion, and the optical endoscope 9 is used to observe the progress of surgery performed using the surgical instrument body 8.

The surgical instrument body 8 is an instrument for incising or coagulating a lesion using, for example, an electric cautery. The surgical instrument body 8 is connected to a power supply unit 11. The power supply unit 11 supplies driving power to the surgical instrument body 8 over a cord or the like, and has the ability to vary the setting of an output value or an output waveform of electric energy according to whether an incision mode or coagulation mode is selected. The surgical instrument body 8 and the power supply unit 11 (or control unit in some instruments) constitute the surgical instrument 20.

The endoscope 9 is, for example, a rigid endoscope having a rigid insertion unit 12. A TV camera 15 having, for example, a charge coupled device (CCD) 14 as an imaging device incorporated therein is mounted on an eyepiece unit 13 located at the back end of the insertion unit 12, whereby a means for producing endoscopic images is realized.

A light guide cable 16 extending from the endoscope 9 is linked to a light source apparatus 17. Illumination light emanating from a lamp, which is not shown, in the light source apparatus 17 is propagated over a light guide contained in the light guide cable 16 and a light guide lying through the endoscope 9. The illumination light is emitted through the end surfaces of the light guides locked in an illumination window formed at the distal end of the insertion unit 12. An object such as an intracavitary organ is thus illuminated.

An objective lens that is not shown is locked in an observation window adjoining the illumination window, and forms an optical image of an object. The optical image is propagated backward along, for example, a system of relay lenses serving as an optical image propagating means located in the insertion unit 12. The optical image can be viewed in enlargement through an eyepiece, which is not shown, included in the eyepiece unit 13.

The propagated optical image is projected on the CCD 14 via an image formation lens 18 included in the TV camera 15 which is mounted on the eyepiece unit 13 so that it can be dismounted freely. The CCD 14 is connected to a camera control unit (hereinafter abbreviated to CCU) over a signal cable 19. A signal photoelectrically converted by the CCD 14 is processed by a video processing circuit 21a included in the CCU 21, whereby a standard video signal is produced and output to a first monitor 22 (via a mixer 21b).

The video signal sent from the CCU 14 is output to the first monitor 22, whereby an endoscopic image representing the intracavitary organ projected on the CCD 14 and the distal part of the surgical instrument body 8 used for surgery is displayed.

Moreover, the CCU 21 and power supply unit 11 are connected to a (first) controller 24 for controlling them.

Figure 3:
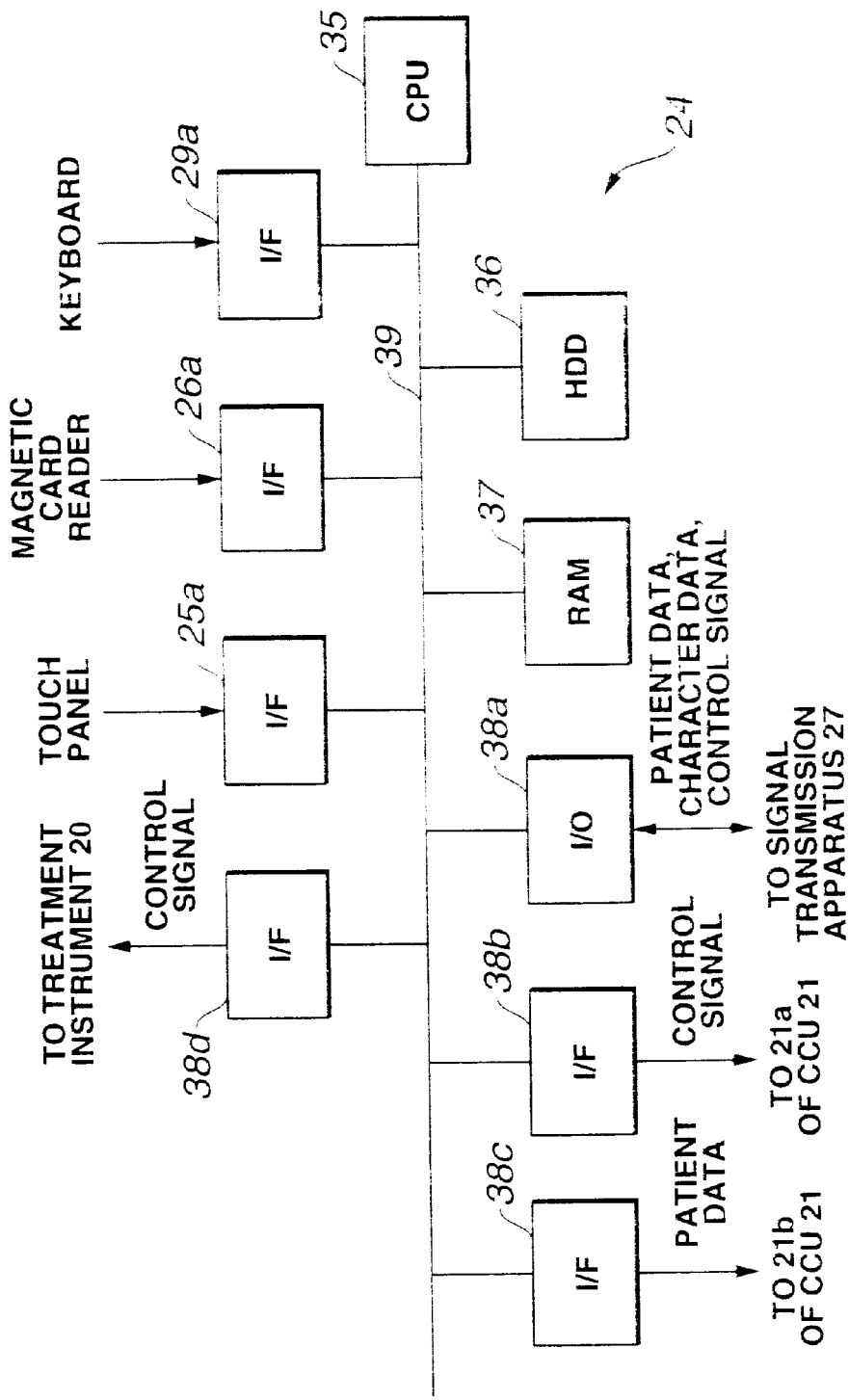

FIG. 3 shows the configuration of the controller 24.

The controller 24 consists mainly of a central processing unit (CPU) 35, a hard disk drive (HDD) 36, a memory 37, and an input/output (I/O) interface 38a. The CPU 35 gives control. The HDD 36 is used to store operation programs according to which the CPU 35 operates. The memory 37 is used to temporarily store an image and used as a work area. The I/O interface 38a allows input or output of control signals or the like via a signal transmission unit 27. The CPU 35, HDD 36, memory 37, and I/O interface 38a are interconnected over a bus 39.

Moreover, a touch panel 25 used to input instructions, a magnetic card reader 26 for inputting patient data or the like, and a keyboard 29 are interconnected over the bus 39 via interfaces 25a, 26a, and 29a respectively.

Moreover, interfaces 38b and 38c are included for outputting control signals and patient data to the video processing circuit 21a and mixer 21b in the CCU 21. Furthermore, an interface 38d is included for outputting the control signals to the power supply unit 11 in the treatment instrument 20.

Assuming that a command or the like is input for changing the tone of endoscopic images using, for example, the touch panel 25, a control signal used to change the tone is output from the controller 24 to a tone setting circuit included in the video processing circuit 21a in the CCU 21. Tone change is thus controlled. Moreover, the power supply unit 11 in the surgical instrument 20 is controlled in order to control output of electric energy to the surgical instrument body 8.

When the surgical instrument body 8 is, for example, an electric cautery, setting of the output level of electrical energy to be supplied for incision or coagulation to the electric cautery can be controlled remotely (with application of a control signal to the power supply unit 11). Moreover, when the treatment instrument 20 is a pneumoperitoneum unit, a set value of pressure can be varied.

The magnetic card reader 26 is used to read patient data recorded on a magnetic card. The patient data is input to the controller 24, and output to the mixer 21b in the CCU 21 via the controller 24. The patient data can thus be superimposed on an endoscopic image.

The CCU 21 and the controller 24 installed in the operating room 5 are connected to the (first) signal transmission apparatus (or signal conversion apparatus) 27. A video signal expressing endoscopic images is output from the CCU 21 to the first monitor 22. The video signal is converted into a signal, which is transmissible over the public line 4 such as an integrated services digital network (ISDN), using the signal transmission apparatus 27. The resultant signal is then transmitted to a (second) signal transmission apparatus (or signal conversion apparatus) 28 in the remote control room 6 over the public line 4.

Moreover, a control signal sent from the controller 24 or patient data is converted into a signal, which is transmissible over the public line 4, using the signal transmission apparatus 27. The resultant signal is then transmitted to the signal transmission apparatus 28 in the remote control room 6 over the public line 4.

Moreover, a signal sent from the signal transmission apparatus 28 in the remote control room 6 to the signal transmission apparatus 27 over the public line 4 is converted (demodulated) into a video signal (corresponding to a signal that has not been converted by the signal transmission apparatus 28). The resultant signal is then output to the second monitor 29 connected to the signal transmission apparatus 27. Consequently, image information sent from the signal transmission apparatus 28 can be displayed on the second monitor 29.

The signal transmission apparatuses 27 and 28 convert an input signal into a transmissible signal, and place the transmissible signal on the public line 4. The signal transmission apparatuses 27 and 28 have the ability to convert (demodulate) an input signal, which has been transmitted over the public line 4, into a signal corresponding to a signal that has not been converted (modulated). In short, the signal transmission apparatuses 27 and 28 realize interface means permitting bi-directional communication over the public line 4.

The keyboard 29 used to input character data or the like is connected to the controller 24. Using the keyboard 29, the character data can be transmitted to a remotely supporting operator or the signal transmission apparatus 28 via the controller 24.

By the way, the remote support system 3 in the remote control room 6 has a third monitor 31 connected to the signal transmission apparatus 28. Endoscopic images sent from, for example, the CCU 21 in the operating room 5 are displayed on the third monitor 31.

The signal transmission apparatus 28 is connected to a (second) controller 32. A display device 33 serving as a fourth monitor is connected to the controller 32. Moreover, an input means used to enter support information, for example, a touch panel or a keyboard 34 is connected to the controller 32. A pointing device that is not shown, such as, a mouse is also connected to the controller 32.

The controller 32 captures an endoscopic image, which is sent from the CCU 21 in the operating room 5 via the signal transmission apparatuses 27 and 28, as a still image. Moreover, patient information sent from the first controller 24 via the signal transmission apparatuses 27 and 28 is input to the controller 32. The controller 32 superimposes the patient information on the endoscopic image and displays the resultant endoscopic image on the display device 33. The keyboard 34 or any other input means is used to enter an indication (for example, a mark indicating a position to be resected or an indication indicating the position of an artery to which attention must be given during resection). The indication is displayed as an overlay on the display device 33. This is intended to provide an operator in the operating room 5 with support information such as instruction information needed for surgery.

Image information or the like to be displayed as an overlay on the display device 33 is transmitted to the second monitor 29 in the operating room 5 via the signal transmission apparatuses 28 and 27. The contents of the image information are then displayed on the display screen of the second monitor 29. An operator in the operating room 5 performs surgery while viewing the image that is displayed on the second monitor 29 and that has the support information entered by the remotely supporting operator overlaid. Thus, surgery can be performed properly.

Figure 4:
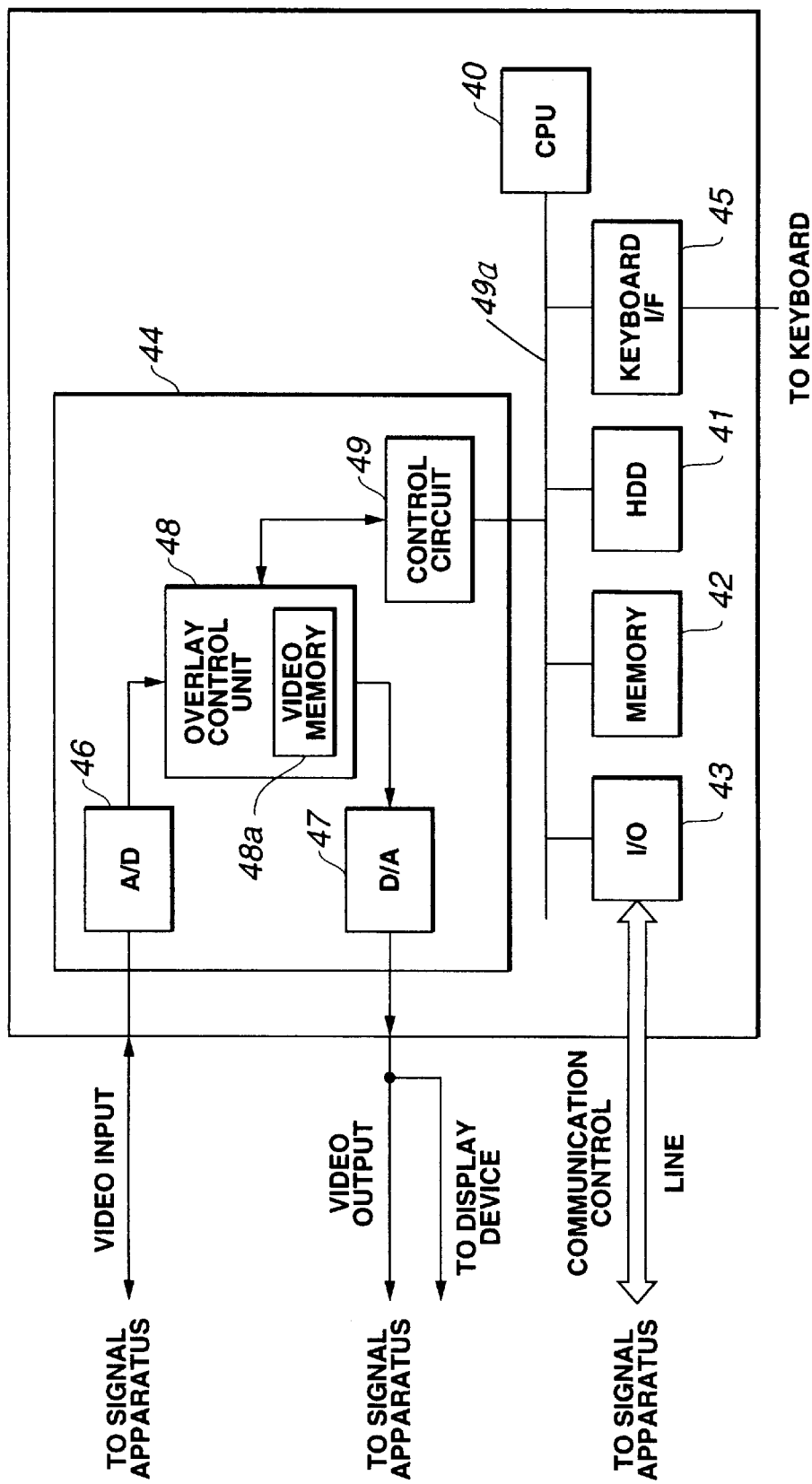

FIG. 4 shows the configuration of the controller 32. The controller 32 consists mainly of a central processing unit (CPU) 40, a hard disk drive (HDD) 41, a memory 42, an input/output (I/O) interface 43, a video capture control unit 44, and a keyboard interface 45. The CPU 40 gives control. The HDD 41 is used to store operation programs according to which the CPU 40 operates, and images. The memory 42 is used to temporarily store an image and used as a work area. The I/O interface 43 permits input or output of control signals or the like via the signal transmission apparatus 28. The video capture control unit 44 captures a video signal and performs superimposition. The keyboard interface 45 is connected to, for example, the keyboard 34. The CPU 40, HDD 41, memory 42, I/O interface 43, capture control unit 44, and keyboard interface 45 are interconnected over a bus.

Communication of a control signal or the like sent from the second signal transmission apparatus 28 is achieved via the I/O interface 43. The operation programs according to which the controller 32 operates are stored in the HDD 41. For example, setting or the like is made for controlling the movement of the surgical instrument 20 at the touch panel 25 in the operating room 5 via the first controller 24. In this case, the contents of control are stored in the memory 42 through the I/O interface 43 in the controller 32 via the signal transmission apparatuses 27 and 28. Moreover, patient information is stored in the memory 43 through the I/O interface 43 in the controller 32.

By the way, the video capture control unit 44 is connected to the signal transmission apparatus 28. The video capture control unit has an A/D converter 46 for digitizing an input video signal and a D/A converter 47 for converting the video signal into an analog form and outputting the analog video signal.

The A/D converter 46 and D/A converter 47 are connected to an overlay control unit 48 for controlling an overlay. The overlay control unit 48 has a video memory 48a in which endoscopic image data or the like is stored. A video signal converted by the A/D converter 46 is stored in the video memory 48a. Otherwise, a video signal stored in the video memory 48a is output to the display device 33 via the D/A converter 47, and then output to the signal transmission apparatus 28.

The video capture control unit 44 is connected to a control circuit 49 for controlling display of an overlay and transmitting or receiving data. The control circuit 49 is connected on a bus.

According to the present embodiment, communication of images by the signal transmission apparatus 28 is achieved via the A/D converter 46 and D/A converter 47 constituting the video capture control unit 44. A video signal input from the A/D converter 46 is converted into image data by the overlay control unit 48 under the control of the control circuit 49.

An output of the overlay control unit 48 is transmitted to the signal transmission apparatus 28 via the D/A converter 47. The CPU 40 controls communication of the signal transmission apparatus 28 with the controller 32 according to a program stored in the HDD 41.

An image captured using the video capture control unit 44 can be stored in the HDD 41. An image stored in the HDD 41 is selected according to an entry made by pressing keys of the keyboard 34 for selecting an image. The CPU 40 outputs a reduced image (thumbnail image) of the selected image to the video capture control unit 44. The reduced image signal may be superimposed on a video signal (sent from the first signal transmission apparatus 27) using the overlay control unit 48.

Images sent from the signal transmission apparatus 28 is converted by the A/D converter 46, and captured by the video capture control unit 44. The image as well as control signals and patient data input via the I/O interface 43 and control circuit 49 can be written in any area in a video memory 48a included in the overlay control unit 48.

A video signal transferred from the D/A converter 47 is also output to the display device 33. The display device 33 can display images like the ones shown in FIG. 5.

A display area 33a on the display device 33 consists of a screen display area 50, a thumbnail display area 51, a state-of-surgical instrument display area 52, a patient information display area 53, and a comment display area 54.

The thumbnail display area 51 is an area in which a plurality of images relevant to a selected item is displayed. For selecting a desired item (patient name, procedure name, or the like), an image selection button (not shown) appearing on a tool bar displayed in the display area 33a is manipulated in order to open an image window.

Displayed in the screen display area 50 are images expressed by a video signal sent from the CCU 21 forming an endoscopic imaging means and an image selected from the thumbnail display area 51.

Displayed in the thumbnail display area 51 are reduced images of image data accumulated in the second controller 32, and a reduced image (thumbnail image) of a still image produced using a video signal that expresses a motion picture or endoscopic images and that is sent from the CCU 21.

Displayed in the state-of-surgical instrument display area 52 are the states of the surgical instrument body 8 and CCU 21 transmitted from the first controller 24.

Displayed in the patient information display area 53 is patient information sent from the first controller 24.

Figure 5:
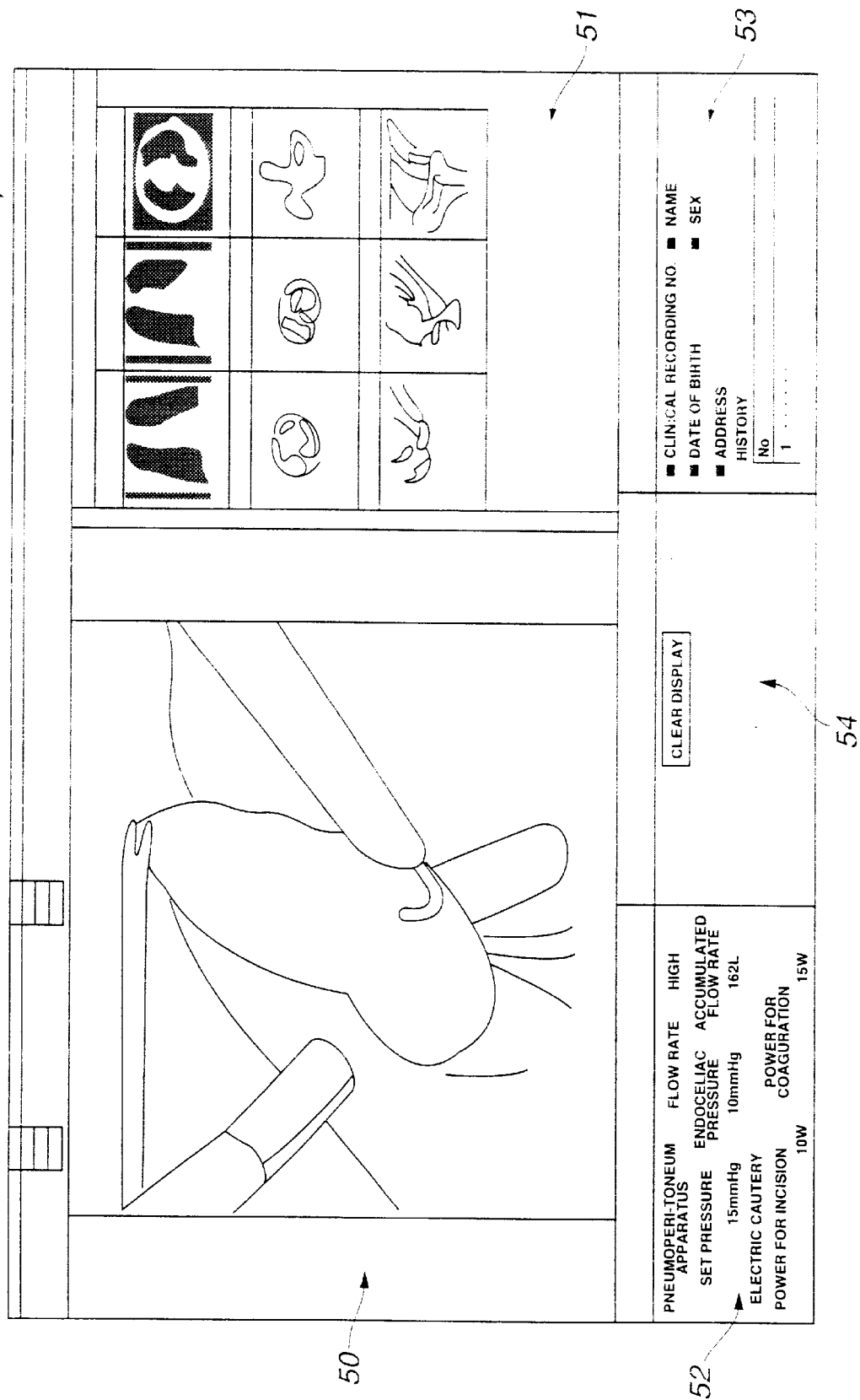

Moreover, a comment transmitted from the surgery system 2 is displayed in the comment display area 54 interposed between the state-of-surgical instrument display area 52 and patient information display area 53 shown in FIG. 5.

Incidentally, the standard H320 and others have been established as a rule for transmitting images, voice, or data over a public line. The standard H320 may be regarded as a standard stipulating transmission of images, voice, or signals over the ISDN.

Operations to be exerted by the present embodiment having the foregoing components will be described below.

As shown in FIG. 1 or FIG. 2, the surgery system 2 and remote support system 3 are linked by the public line 4 such as the ISDN. The power supplies of the surgery system 2 and remote support system 3 are then turned on.

Moreover, patient information including the name of the patient 7 is input from the magnetic card reader 26 to the first controller 24.

The endoscope 9 is connected to the light source apparatus 17 over the light guide cable 16 so that illumination light can be supplied through the endoscope 9. Moreover, the TV camera 15 is mounted on the eyepiece unit 13 of the endoscope 9. The signal cable 19 extending from the TV camera 15 is linked to the CCU 21, so that an endoscope image projected on the CCD 14 can be displayed on the first monitor 22.

A pneumoperitoneum unit is thrust into the abdominal cavity of the patient 7 by way of a trocar and cannula that is not shown, whereby air is supplied to the abdominal cavity. In this case, the set value of a flow rate at which air is supplied to the abdominal cavity is entered at the keyboard 29 or the like.

The insertion unit 12 of the endoscope 9 is thrust by way of the trocar and cannula, so that an image of a lesion in the abdominal cavity can be displayed on the first monitor 22.

The surgical instrument body 8 such as an electric cautery used for surgery is thrust into the abdominal cavity of the patient 7 by way of the trocar and cannula. The output value of electrical energy to be supplied to the electric cautery for incision or coagulation is entered at the keyboard 29 or the like. The contents of control to be given for surgery are thus entered.

For changing the tone of endoscopic images displayed on the first monitor 22, a control signal is sent from the first controller 24 to the CCU 21 by manipulating the touch panel 25. Thus, the tone can be changed.

A video signal output from the CCU 21 to the first monitor 22 and expressing endoscopic images is transmitted from the first signal transmission apparatus 27 to the second signal transmission apparatus 28 over the public line 4, and then visualized on the third monitor 31.

The video signal can be input to the second controller 32. When an endoscopic image displayed on the third monitor 31 properly represents a region to be resected during surgery, the remotely supporting operator gives instructions at the keyboard 34. The endoscopic image (still image) is then captured using the video capture control unit 44 in the controller 32. The captured endoscopic image is, as shown in FIG. 5, then displayed in the screen display area 50 on the display device 33 connected to the controller 32.

Patient information read by the magnetic card reader 26 is input from the first controller 24 to the controller 32 through the I/O interface 43 via the signal transmission apparatuses 27 and 28. The patient information is stored in, for example, the memory 42 in the controller 32, and, as shown in FIG. 5, displayed in the patient information display area 53 on the display device 33 all the time.

The remotely supporting operator displays the endoscopic image sent from the operating room 5 with the patient information overlaid. When the surgical instrument body 8 is used to resect a lesion, the position of a region to be resected is marked on a still image. A mouse or the keyboard 34 that is not shown is used to enter a mark on the still image. If attention must be given to an artery located near the region to be resected, the artery is marked in a color different from the color of the mark indicating the position of the region to be resected. Support information is thus displayed.

When an electric cautery is used to incise or coagulate a lesion, the operator in the operating room 5 enters the set value of electric energy at the touch panel 25. The contents of control including the setting of electric energy output to the surgical instrument 20 are sent from the first controller 24 to the I/O interface 43 of the second controller 32, and stored in, for example, the memory 42. Moreover, control information (setting information) concerning the surgical instrument 20 is, as shown in FIG. 5, displayed in the state-of-surgical instrument display area 52.

Referring to FIG. 5, setting information of a pneumoperitoneum unit is also displayed in the state-of-surgical instrument display area 52. Namely, control information concerning a plurality of surgical instruments can be displayed.

When the operator in the operating room 5 changes the output value of electric energy supplied to an electric cautery at the touch panel 25, the changed contents are sent to the I/O interface 43 in the second controller 32 and displayed in the state-of-surgical instrument display area 52. The contents of control (setting) given to the surgical instrument 20 are displayed on the display device 33 nearly in real time. The remotely supporting operator can check the state of the surgical instrument 20 nearly in real time.

Moreover, when the operator in the operating room 5 has a comment on what he/she has noticed about surgery, the operator enters the comment at the keyboard or the like. The comment is, as shown in FIG. 5, displayed in the comment display area 54.

When the comment is requested to be replied by the remotely supporting operator, a reply is sent to the operating room 5. The operator in the operating room 5 can acknowledge the reply by looking at the second monitor 29.

The remotely supporting operator can record an endoscopic image captured by the video capture control unit 44. When a recording instruction is given at the keyboard 34, a still image is recorded in the HDD 41.

Selected reduced images made by reducing in size any of endoscopic images accumulated in the HDD 41 can be displayed in the thumbnail display area 51 shown in FIG. 5.

Aside from the endoscopic images, radiographic images of the patient 7 can be transmitted from the first controller 24 to the second controller 32 in the remote control room 6. Reduced images of any of radiographic images accumulated in the HDD 41 can be displayed.

For performing surgery on the patient 7, the remotely supporting operator can make proper diagnosis by referencing the images on the display device 33. The remotely supporting operator can provide the operating room 5 with support information helpful in the surgery according to the diagnosis.

Image information displayed as an overlay on the display device 33 is displayed on the second monitor 29 via the signal transmission apparatuses 28 and 27. The operator in the operating room 5 carries out a surgical procedure with reference to the contents of display on the second monitor 29 including the support information. The operator in the operating room 5 can thus accomplish the surgical procedure properly.

Figure 6:
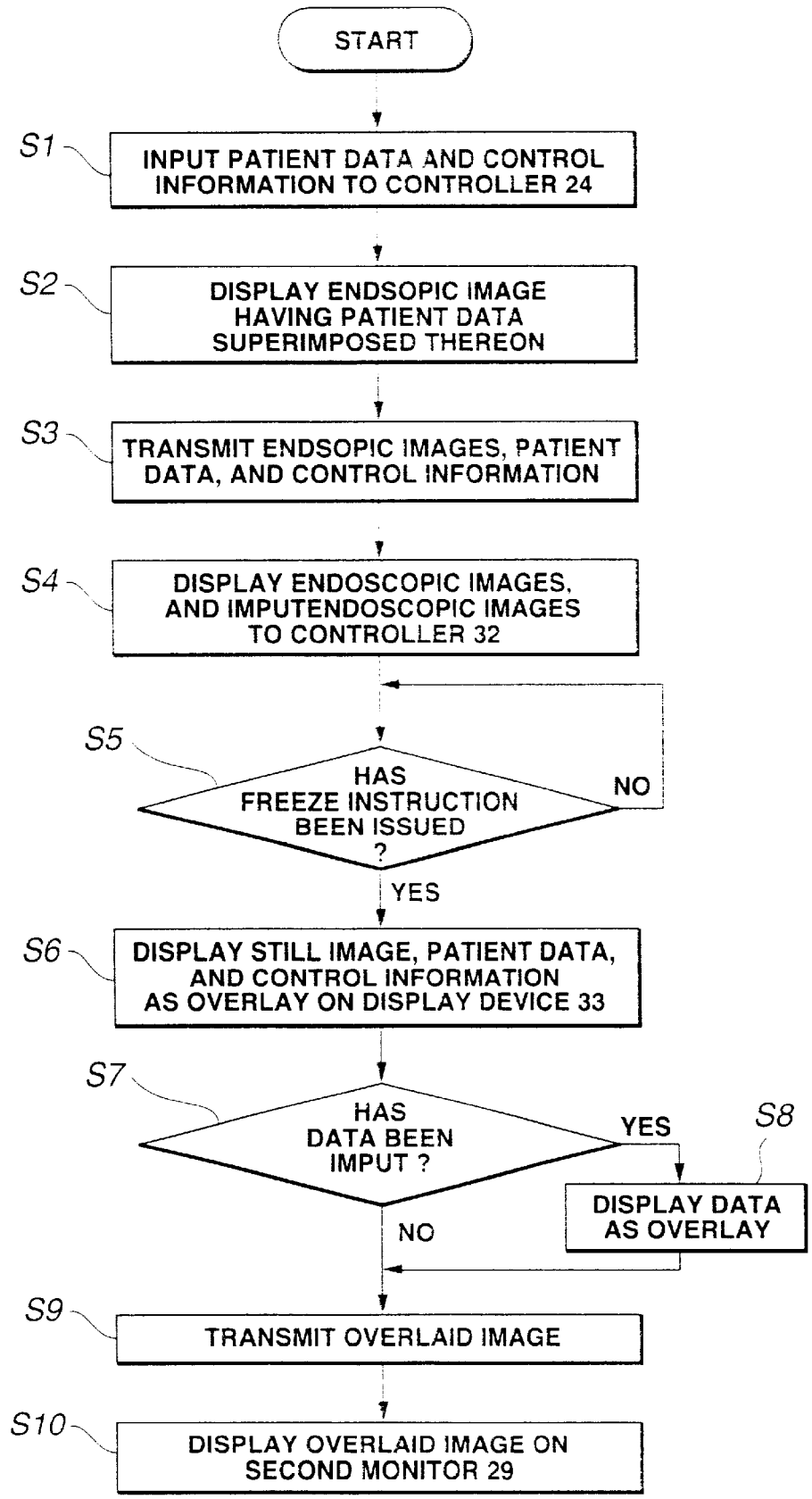

According to the present embodiment, as described in the flowchart of FIG. 6, surgical information acquired in the operating room 5 can be displayed in the remote control room 6.

Specifically, the power supplies of the systems 2 and 3 are turned on. At step S1, patient data of the patient 7 undergoing surgery and control information used to control the surgical instrument 20 are input to the controller 24. At step S2, endoscopic images having the patient data superimposed thereon are displayed on the first monitor 22.

At step S3, the endoscopic images having the patient data superimposed thereon are transmitted from the CCU 24 to the signal transmission apparatus 28 in the remote control room 6 via the signal transmission apparatus 27 over the public line 4. The patient data and control information input to the controller 24 are transmitted to the signal transmission apparatus 28 in the remote control room 6 via the signal transmission apparatus 27 over the public line 4.

At step S4, the endoscopic images having the patient data superimposed thereon are displayed on the third monitor 31. Moreover, the endoscopic images, patient data, and control signal are input to the controller 32.

The keyboard 34 is used to instruct capture of a still image. A still image of any of the endoscopic images input to the controller 32 is fetched into the video capture control unit 44, and displayed on the display device 33 as shown in FIG. 5 (step S6).

The patient data and the contents of control given to the surgical instrument 20 are displayed on the display device at the same time.

When it is judged at step S7 whether data has been input, if the remotely supporting operator enters support data at the keyboard 34 or the like, the data is overlaid (step S8). The data-overlaid image displayed on the display device 33 is transmitted to the operating room 5 (step S9), and then displayed on the second monitor 29 (step S10).

According to the present embodiment, the remotely supporting operator can view images showing a surgical scene nearly in real time on the third monitor 31. By looking at the display device 33, the remotely supporting operator can check the state of the surgical instrument 20 in the operating room 5 nearly in real time at any time, and also check patient information. In case of not only ordinary surgery but also emergency surgery, the remotely supporting operator can grasp the state of the surgical instrument 20 and the patient information at any time. The remotely supporting operator can therefore quickly provide the operator in the operating room 5 with support information helpful in carrying out a proper surgical procedure. The operator in the operating room 5 can reference the support information and carry out a surgical procedure smoothly and quickly however complicated the surgical procedure is.

The optical endoscope 9 is not limited to the type using a system of relay lenses to propagate an optical image. A type of optical endoscope adopting an image guide in which a fiber bundle is used to propagate an optical image will do. The operator in the operating room 5 and the remotely supporting operator in the remote control room 6 can mutually transfer a voice signal, though it is not illustrated.

Figure 7:
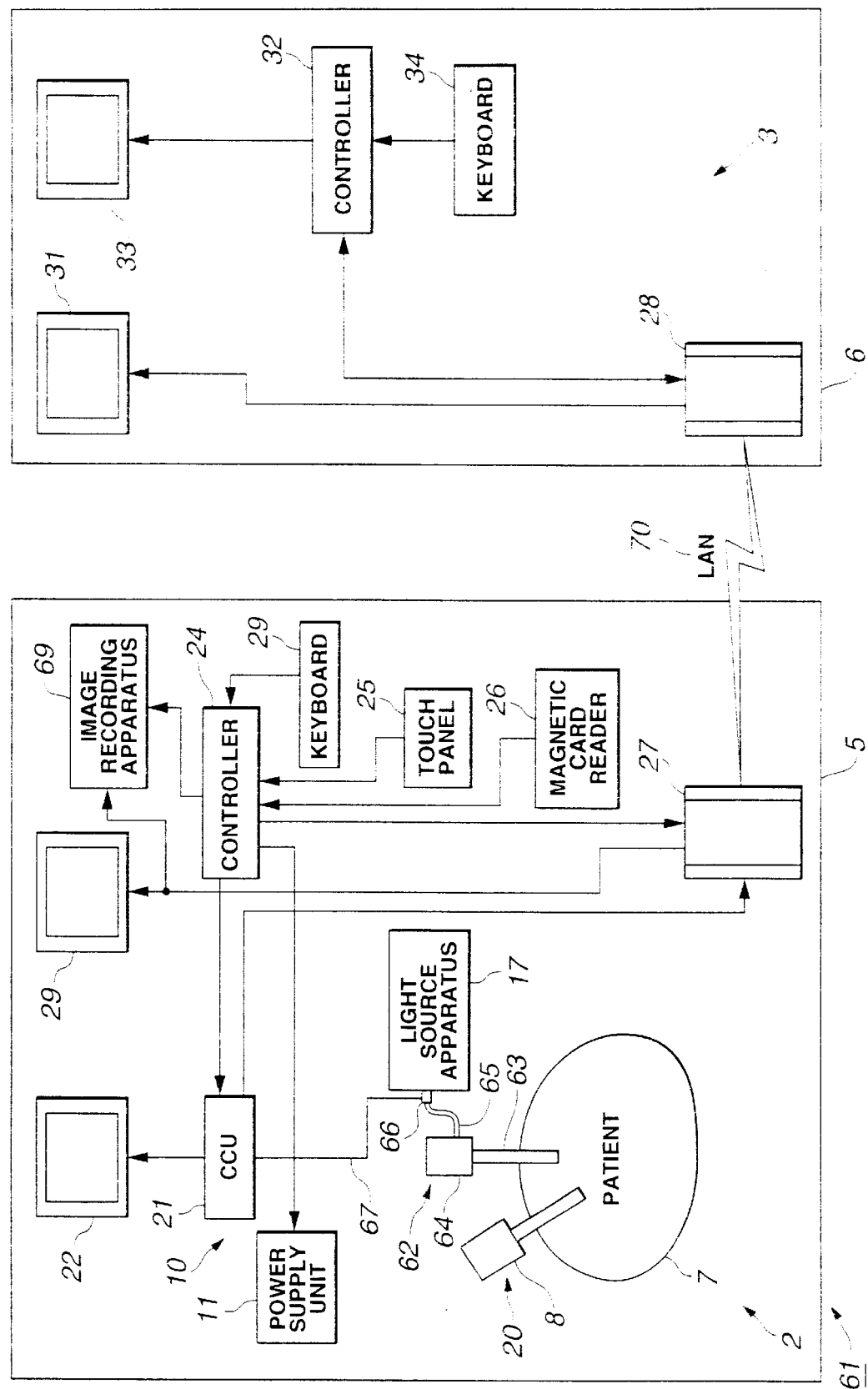
FIG. 7 shows the overall configuration of a remote surgery support system in accordance with the second embodiment of the present invention.

Next, the second embodiment of the present invention will be described with reference to FIG. 7.

Compared with the first embodiment, the present embodiment adopts an electronic endoscope 62 with a built-in imaging device instead of the optical endoscope 9 and TV camera 15 included in the endoscopic imaging apparatus 10 in the surgery system 2.

The electronic endoscope 62 has an insertion unit 63, an operation unit 64 formed at the back end of the insertion unit 63, and a universal cord 65 extending from the operation unit 64. A connector 66 attached to the end of the universal cord 65 is plugged into the light source apparatus 17, whereby illumination light is supplied from the light source apparatus 17.

An imaging device that is not shown is incorporated in the distal part of the insertion unit 63. The imaging device is connected to the CCU 21 over a signal line 67 linked to the connector 66.

A video signal output to the second monitor 29 is also input to an image recording apparatus 69. When a recording instruction is input to the controller 24 using the touch panel 25, an image desired to be recorded can be recorded.

In the operating room 5, information including the support information given by the remotely supporting operator during surgery may be referenced as material for cure after surgery or utilized as significant material for future surgery.

According to the present embodiment, a local area network (LAN) 70 is adopted as a communication line linking the surgery system 2 and the remote support system 3 employed in the first embodiment on behalf of the public line 4.

The other components are identical to those of the first embodiment.

Operations to be exerted by the present embodiment are nearly identical to those by the first embodiment.

Incidentally, when a remotely supporting operator needs radiographic images or the like in addition to endoscopic images so as to evaluate a patient's condition, the image information may be transferred from the controller 24 in the operating room 5 to the controller 32 (HDD 41 therein) in the remote control room 6.

Next, the third embodiment of the present invention will be described with reference to FIG. 8. Compared with the endoscope system 1 of the first embodiment, a system of the present embodiment does not have the third monitor 31 installed in the remote control room 6 but uses the display device 33 to display the contents of display on the third monitor 31.

Figure 8:
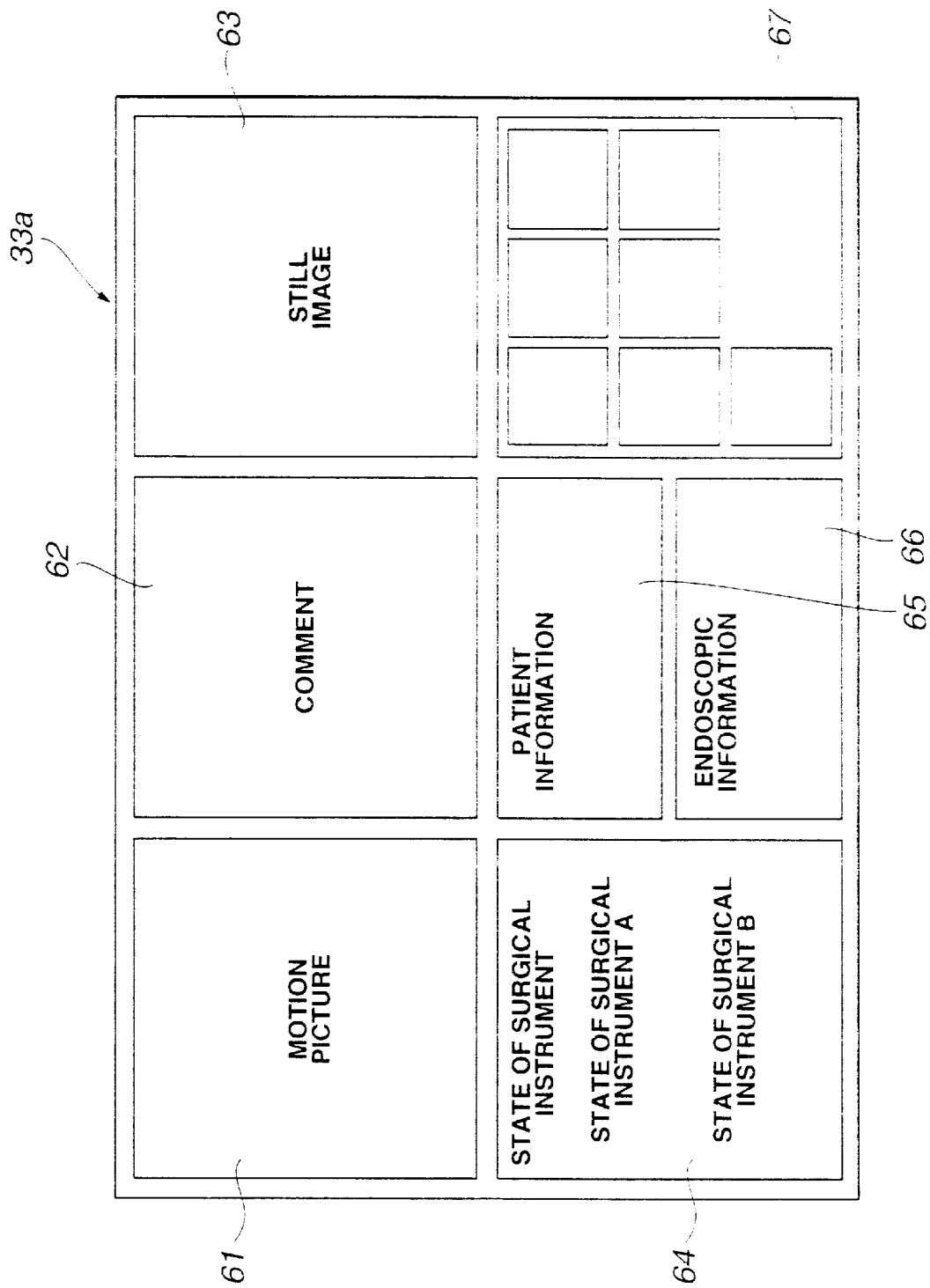
FIG. 8 shows the contents of display on a display screen of a display device in accordance with the third embodiment of the present invention.

FIG. 8 shows a practical example of the contents of display on the display screen 33a of the display device 33 in the present embodiment.

As shown in FIG. 8, the display screen 33a of the display device 33 has a motion picture display area 61, a comment display area 62, a still image display area 63, a state-of-surgical instrument display area 64, a patient information display area 65, an endoscopic information display area 66, and a thumbnail image display area 67. The motion picture display area 61 is used to display an endoscopic motion image. The comment display area 62 is used to display character information. The still image display area 63 is used to display a captured still image. The state-of-surgical instrument display area 64 is used to display the state of a surgical instrument. The patient information display area 65 is used to display patient information. The endoscopic information display area 66 is used to display information of an endoscope, for example, the state of the light source apparatus set for illumination or the state of the imaging device set for signal processing. The thumbnail image display area 67 is used to display thumbnail images.

According to the present embodiment, for example, the first monitor 22 has the motion picture display area 61, state-of-surgical instrument display area 64, patient information display area 65, and endoscopic information display area 66 that are shown in FIG. 8. These areas are used to display a motion picture of endoscopic images, the state of a surgical instrument, patient information, and endoscopic information respectively.

On the first monitor 22, endoscopic images expressed with a signal processed by the CCU 21 are displayed in the motion picture display area 61. The state of a surgical instrument set using the controller 24 is displayed in the state-of-surgical instrument display area 64. Patient information input from the magnetic card reader 26 via the controller 24 is displayed in the patient information display area 65. Moreover, endoscopic information sent from the controller 24 is displayed in the endoscopic information display area 66. The endoscopic information includes the situation of setting concerning a tone and others made for signal processing performed by the CCU 21, and the situation of setting made for adjusting light emanating from the light source apparatus.

The contents of display on the first monitor 22 are input from the CCU 21 to the controller 32 via the signal transmission apparatus 27 and the signal transmission apparatus 28 in the remote control room 6. The same contents of display as those on the first monitor 22 are displayed on the display device 33.

When the operator in the operating room 5 has a comment that must be sent to the remote control room 6, the operator enters the comment at the keyboard 29. The comment is then sent from the controller 24 to the controller 32 via the signal processing apparatus 27 and the signal processing apparatus 28 in the remote control room 6. The contents of the comment are displayed in the comment display area 62 on the display device 33.

In the remote control room 6, when a motion picture displayed on the display device 33 contains an image that must be captured, a capture instruction is entered at the keyboard 34 connected to the controller 32. The image is then captured as a still image, and the still image is displayed in the still image display area 62.

A mark indicating a region to be resected may be appended to the still image displayed in the still image display area 63.

For displaying a thumbnail image of any of images accumulated in the HDD 41, a thumbnail image display instruction is entered. The thumbnail image is then displayed in the thumbnail image display area 63. Moreover, a reply comment may be entered relative to a comment displayed in the comment display area 67.

Moreover, a comment such as a note explaining what should be attracted attention during resection may be entered.

Among the contents of display on the display device 33, image information including a still image displayed in the still image display area 62 and the contents of a comment displayed in the comment display area 67 are sent to the controller 32 via the signal transmission apparatus 28 and the signal transmission apparatus 27 in the operating room 5. The image information including the still image and the comment are then displayed on the second monitor 29.

The operator in the operating room 5 looks at the second monitor 29 displaying the support information sent from the remote control room 6, and carries out a surgical procedure such as resection.

When a plurality of surgical instruments is employed, the states of the plurality of surgical instruments A and B are, as shown in FIG. 8, displayed in the state-of-surgical instrument display area 64.

According to the present embodiment, an endoscopic image, the state of a surgical instrument, patient information, and endoscopic information that are the same as those displayed in the operating room 5 can be displayed on the display device 33 in the remote control room 6 all the time. Setting or controlled states of almost all electric equipment employed in a surgical procedure performed under endoscopic observation in the operating room 5 can be checked in the remote control room 6 all the time.

For example, the contents of setting concerning a surgical instrument may be modified using the touch panel 25. In this case, modified information is sent from the controller 24 to the CCU 21. The set state of the surgical instrument displayed in the state-of-surgical instrument display area 62 on the first monitor 22 is then modified and displayed. The set state of the surgical instrument appended to image information sent from the CCU 21 to the remote control room 6 via the signal transmission apparatus 27 is also modified. The set state of the surgical instrument displayed in the state-of-surgical instrument display area 64 on the display device 33 is also modified. In the remote control room 6, information set in the operating room 5 is available nearly in real time (without the necessity of performing any manipulation for acquiring needed information).

Moreover, the operator in the operating room 5 can carry out a surgical procedure while taking account of information displayed on the second monitor 29 and viewing endoscopic images displayed on the first monitor 22.

The present embodiment has nearly the same advantages as the first embodiment.

Incidentally, patient information may be displayed in the comment display area 62. Endoscopic information may not be displayed on the first monitor 22 but may be sent from the controller 24 to the remote control room 6. In the remote control room 6, information items to be displayed may be able to be selected.

Moreover, a motion picture, the state of a surgical instrument, and patient information displayed on the first monitor 2 may be sent to the remote control room 6 and displayed on, for example, the third monitor 31. The other items of support information, that is, a still image and others may be displayed on the display device 33.

Specifically, endoscopic images, the state of a surgical instrument, and patient information that are the same as those displayed on the first monitor 22 in the operating room 5 may be displayed in the remote control room 6 as they are.

In the remote control room 6, when more support information must be appended to these information items, a still image (containing information such as a mark) and thumbnail images displayed on the display device 33 are referenced. Then, a support image that is the still image having a mark appended thereto or support information including a comment may be sent to the operating room 5 and displayed on the second monitor 29.

Depending on whether the operating room 5 and remote control room 6 are linked by the public line 4, control of display can be simplified. In either case, a display format according to which information is displayed on the first monitor 22 remains unchanged. The operator in the operating room 5 will therefore not be upset but be able to carry out a surgical procedure smoothly while referencing data displayed in the same display format.

Moreover, even in the remote control room 6, endoscopic images, the state of a surgical instrument, and patient information which are arranged in the same display format as they are on the first monitor 22 in the operating room 5 can always be referenced on the third monitor 31.

In the aforesaid embodiments, the remotely supporting operator may be permitted to set an output value of electric energy supplied to an electric cautery or enter control information used to control the movement of a surgical instrument. Specifically, in cases where the remotely supporting operator can set a more proper value more readily, the remotely supporting operator may be permitted to send a control signal from the controller 32 to the controller 24 in the operating room 5 using the keyboard 34 or touch panel. The movement of the surgical instrument 20 may be controlled based on the control signal.

Moreover, as for the aforesaid embodiments, it has been described that endoscopic images output from the CCU 21 are displayed on the first monitor 22. Alternatively, control information used to control a treatment instrument and patient information may be input from the controller 24 and superimposed on the endoscopic images.

Next, the fourth embodiment of the present invention will be described with reference to FIG. 9 and FIG. 10.

Figure 9:
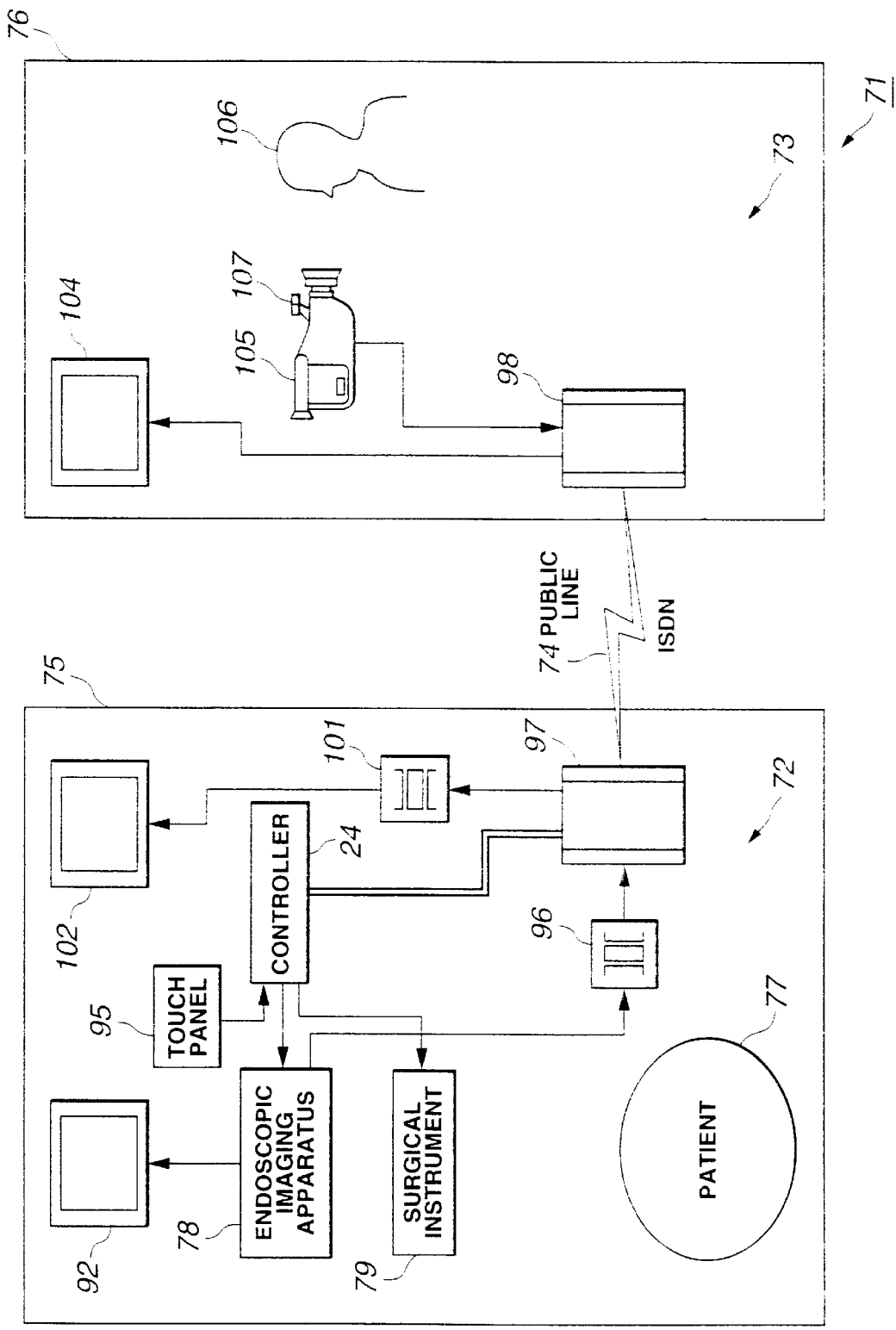
FIG. 9 and FIG. 10 relate to the fourth embodiment of the present invention.
Figure 10:
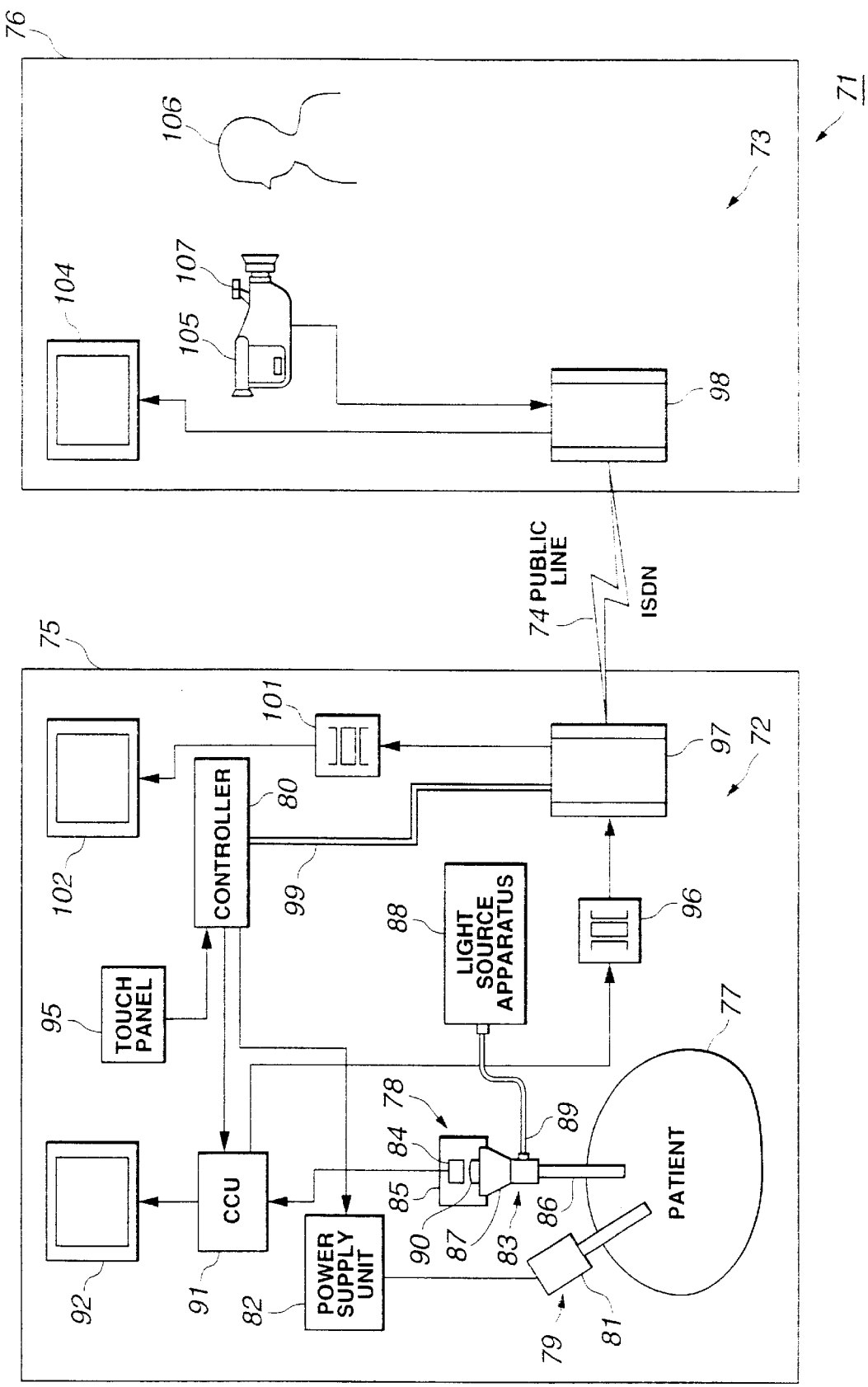

A remote surgery support system 71 in accordance with the fourth embodiment of the present invention shown in FIG. 9 and FIG. 10 has a surgery system 72 and a remote support system 73 linked by a public line 72 such as the integrated services digital network (ISDN). The remote support system 73 is located remotely to the surgery system 72. The surgery system 72 and remote support system 73 are installed in an operating room 75 and a remote room 76 (or a remote control room) respectively.

The surgery system 72 installed in the operating room 75 has an endoscopic imaging apparatus 78 used to observe a patient 77 using an endoscope and a surgical instrument 79 used to perform surgery under the endoscopic observation. The surgical instrument 79 may be an electric cautery, a pneumoperitoneum unit, or an ultrasonic surgical instrument.

The endoscopic imaging apparatus 78 and surgical instrument 79 are connected to a (first) controller 80 for controlling them.

To be more specific, the surgical instrument 79 has, as shown in FIG. 10, a surgical instrument body 81 such as an electric cautery, and a power supply unit 82 for supplying operating power to the surgical instrument body 81. The surgical instrument body 81 is thrust into the abdominal cavity of the patient 77 in order to perform surgery for cure.

The endoscopic imaging apparatus 78 has an optical endoscope 83 used to observe a surgical scene. A TV camera 85 with a built-in solid-state imaging device, for example, a built-in charge coupled device (CCD) 84 is mounted on the endoscope 83, whereby an endoscopic imaging means for producing endoscopic images is realized.

According to the present embodiment, the endoscope 83 is, for example, a rigid endoscope having a rigid insertion unit 86. The TV camera 85 is mounted on an eyepiece unit 87 formed at the back end of the insertion unit 86 so that the TV camera can be dismounted freely.

The endoscope 83 is connected to a light source apparatus 88 over a light guide cable 89. Illumination light emanating from a lamp, which is not shown, included in the light source apparatus 88 is propagated over a light guide contained in the light guide cable 89 and a light guide running through the endoscope 83. The propagated illumination light is emitted from the distal end surfaces of the light guides locked in an illumination window formed at the distal end of the insertion unit 87. An object such as an intracavitary organ is thus illuminated.

An objective lens that is not shown is locked in an observation window adjoining the illumination window, and forms an optical image of the object. The optical image is propagated backward along an optical image propagating means incorporated in the insertion unit 84, for example, a system of relay lenses. Consequently, the image of the object can be viewed in enlargement through an eyepiece, which is not shown, included in the eyepiece unit 87 formed at the back end of a hand-held portion to be held by an operator. The optical image propagating means incorporated in the endoscope 83 may be an image guide formed with a fiber bundle aside from the system of relay lenses.

An propagated optical image is projected on the CCD 84 via an image formation lens 90 of the TV camera 85 which is mounted on the eyepiece unit 87 so that the TV camera can be dismounted freely. The CCD 84 is connected to a camera control unit (CCU) 91 over a signal cable. A signal photoelectrically converted by the CCD 84 is processed in order to produce a standard video signal. The video signal is then output to the first monitor 92. Consequently, endoscopic images representing an intracavitary organ and the distal part of the surgical instrument body 11 used to perform surgery on the organ and being projected on the CCD 84 are displayed on the first monitor 92.

Moreover, the CCU 91 and power supply unit 82 are connected to a controller 80 for controlling them.

The controller 80 is also connected to a touch panel 95 or the like used to enter an instruction of a control operation and to a magnetic card reader or the like, which is not shown, for inputting patient data.

The touch panel 95 may be used to control the CCU 91 via the controller 80 so as to change tones or the like. Moreover, the movement of the surgical instrument body 81 of the surgical instrument 79 may be controlled using the touch panel 95. When the surgical instrument body 81 is, for example, an electric cautery, the output level of electric energy supplied from the power supply 82 to the electric cautery for the purpose of incision or coagulation can be set using the touch panel 95.

According to the present embodiment, the CCU 91 included in the endoscopic imaging apparatus 78 is connected to a (first) image transmission apparatus 97 serving as a signal transmitting means via a signal isolating means, for example, a video transformer 96. Specifically, endoscopic images produced by the endoscopic imaging apparatus 78 are converted into a video signal using the CCU 91. The video signal is applied to the primary winding of the video transformer 96 enabling transmission of a signal having frequency components in a wide frequency band. The secondary winding of the video transformer 96 is connected to the image transmission apparatus 97. Thus, the video signal is supplied to the image transmission apparatus 97 with the electrical isolation between the CCU 91 and image transmission apparatus 97 maintained.

The image transmission apparatus 97 converts the video signal, which is input from the CCU 91, into a signal transmissible over the public line 74, so that the signal can be transmitted to a (second) image transmission apparatus 98 in the remote control room 76 over the public line 74. The image transmission apparatuses 97 and 98 can transmit an image signal having frequency components in a wide frequency band. A control signal or voice signal having lower frequency components can therefore be transmitted in general.

Moreover, the controller 80 in the operating room 75 is connected to the image transmission apparatus 97 via signal isolating means, for example, optical modems 99. The optical modems 99 in the controller 80 and image transmission apparatus 97 respectively are linked by an optical cable. A converter for converting an electric signal into an optical signal is attached to the end of the optical cable coupled to the controller 80. A converter for converting the optical signal into the electric signal is attached to the end of the optical cable coupled to the image transmission apparatus 97. The controller 80 is connected to the image transmission apparatus 97 via the signal isolating means.

The image transmission apparatus 97 converts a signal, which has been sent from the image transmission apparatus 98 in the remote control room 76 to the image transmission apparatus 97 over the public line 74, into a video signal. The video signal is output to the second monitor 102 (isolated from the image transmission apparatus 97) via a second video transformer 101 connected to the image transmission apparatus 97. Image information sent from the image transmission apparatus 98 can be displayed on a second monitor 102. The second monitor 102 is connected to the image transmission apparatus 97 via the signal isolating means.

A control signal used to control the surgical instrument 79 and sent from the controller 80, or patient data read with a magnetic card reader and input to the controller 80 are input to the image transmission apparatus 97 via the optical modems 99. The image transmission apparatus 97 converts the input signal into a signal transmissible over the public line 74, and transmits the resultant signal to the image transmission apparatus 98 in the remote room 76 over the public line 74.

According to the present embodiment, electric equipment are connected to the image transmission apparatus 97 in the operating room 75 via the signal isolating means. Supposing the public line 74 is struck by lightning, the electric equipment connected to the image transmission apparatus 97 can be protected from being damaged. This eliminates the possibility that an operator using the electric equipment to carry out a surgical procedure and the patient 77 undergoing surgery performed using the treatment instrument 79 may get an electric shock. Thus, safety is ensured.

Patient data read from a magnetic card using a magnetic card reader is input to the controller 80. The controller 80 may output the patient data to the CCU 91 so that the patient data will be superimposed on endoscopic images. Otherwise, the controller 80 may output the contents of control to be given to the surgical instrument 79 to the CCU 91 so that the controlled (set) state of the surgical instrument 79 will be superimposed on endoscopic images.

The remote support system 73 in the remote room 76 has a third monitor 104 connected to the image transmission apparatus 98. Endoscopic images or the like sent from the operating room 75 are displayed on the third monitor 104.

Moreover, the image transmission apparatus 98 is connected to an indoor camera 105. A video signal produced by the indoor camera 105 is output to the second monitor 102 via the image transmission apparatuses 98 and 97 over the public line 74. The video signal expresses a remotely supporting operator 106, or a material or explanatory diagram indicating a region to be resected during surgery. The region to be resected is indicated by the remotely supporting operator 106.

A voice microphone 107 is attached to the indoor camera 105. A voice signal originating from the remotely supporting operator 106 is therefore transmitted to the operating room 75, and reproduced with a loudspeaker, which is not shown, included in the second monitor 102. Thus, the remotely supporting operator 106 can give advises or the like to an operator, which is not shown, in the operating room 75 during surgery.

Next, actions to be made in accordance with the present embodiment will be described.

The image transmission apparatuses 97 and 98 are electrically connected over the public line 74. On receipt of a video signal representing endoscopic images sent from the CCU 91 or a control signal and patient data sent from the controller 77, the image transmission apparatus 97 converts the input signal into a signal transmissible over the public line 74. The resultant signal is transmitted to the image transmission apparatus 98 in the remote control room 76 over the public line 74. The image transmission apparatus 98 converts the received signal that has been transmitted over the public line 74, and outputs a resultant signal to the third monitor 104. The endoscopic images and the contents of control to be given to the surgical instrument 79 and the patient data are displayed on the third monitor 104.

Moreover, the indoor camera 105 is connected to the image transmission apparatus 98. The indoor camera 105 images the remotely supporting operator 106 in the remote control room 76 or an explanatory diagram used for surgery. The image transmission apparatus 98 converts the image signal into a signal transmissible over the public line 74, and transmits the resultant signal to the image transmission apparatus 97 in the operating room 75 over the public line 74.

Images produced by the indoor camera 105 are displayed on the second monitor 102 via the image transmission apparatus 97 and video transformer 101. Verbal advises given by the remotely supporting operator 106 are also transmitted in the same manner, and reproduced with a loudspeaker, which is not shown, together with the images displayed on the display screen of the second monitor 102.

The operator in the operating room 75 can carry out a surgical procedure properly owing to the images displayed on the second monitor 102 and support such as the advises received along with the images.

Owing to the foregoing components and operations, for example, even if the public line 74 is struck by lightning, the first monitor 92, second monitor 102, CCU 91, and controller 80 can be protected from being damaged. This is because the electric equipment connected to the image transmission apparatus 97 in the operating room 75 are electrically isolated due to the video transformers 96 and 101 and the optical modems 99. Consequently, the possibility that an operator handling the electric equipment and the patient 77 connected to the electric equipment may get an electric shock can be eliminated reliably.

According to the present embodiment, even if the public line 74 is struck by lightning, since the electric equipment connected to the image transmission apparatus in the operating room 73 are electrically isolated from one another, the electric equipment can be protected from being damaged. Moreover, the possibility that the patient 77 and operator may get an electric shock can be eliminated reliably.

Incidentally, photocouplers or the like may be adopted as the signal isolating means instead of the video transformers 96 and 101, and a video signal or the like may thus be transmitted.

The endoscopic imaging apparatus 78 in accordance with the present embodiment has an endoscope with an external TV camera having the TV camera 85 with the built-in CCD 84 mounted on the optical endoscope 83. The present invention can also be adapted to an electronic endoscope having the CCD 84 incorporated in the distal part of an insertion unit thereof.

Figure 11:
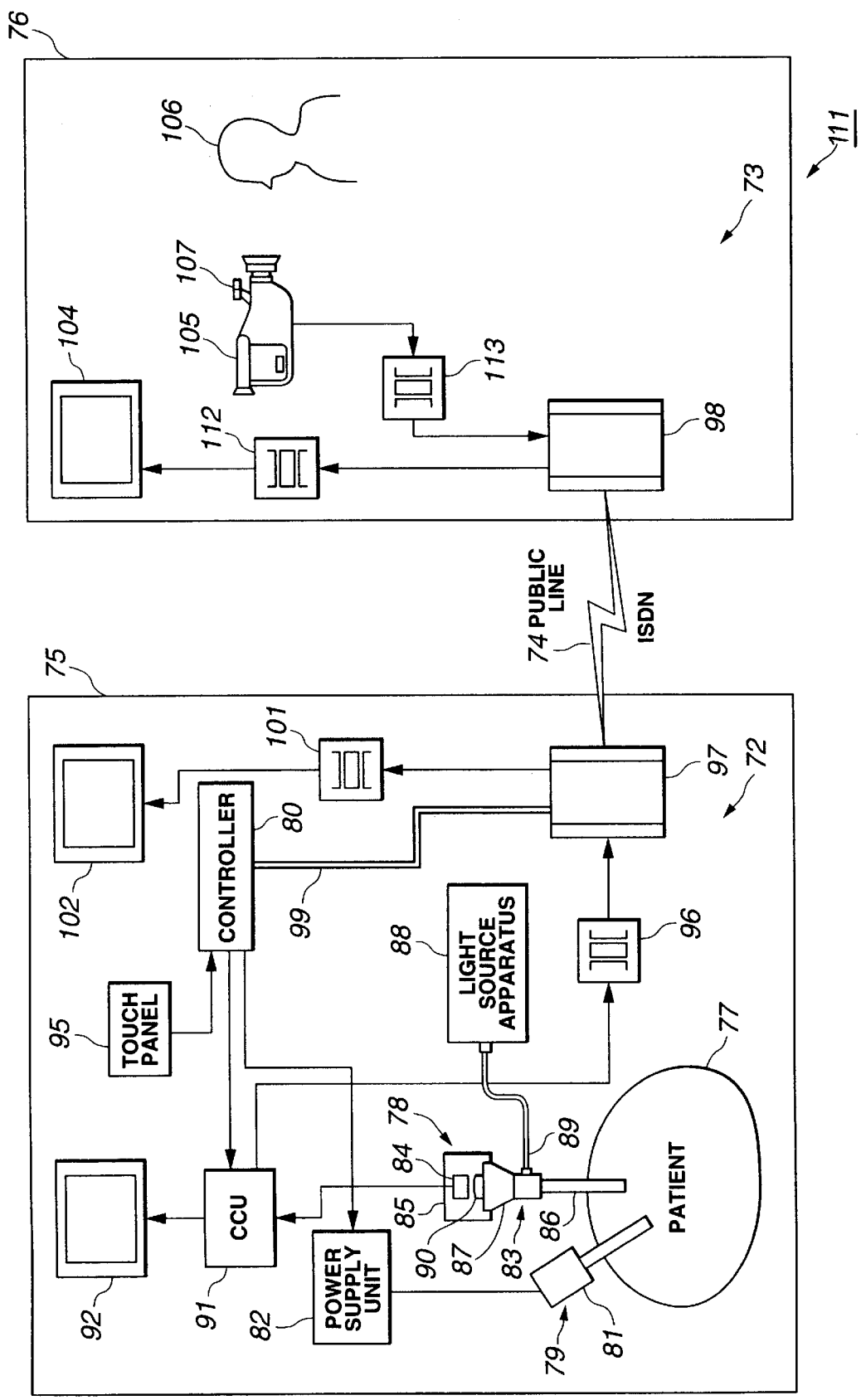
FIG. 11 shows the overall configuration of a remote surgery support system in accordance with the fifth embodiment of the present invention.

Next, the fifth embodiment of the present invention will be described with reference to FIG. 11. FIG. 11 shows the configuration of a remote surgery support system 111 in accordance with the fifth embodiment of the present invention. The remote surgery support system 111 has the electric equipment connected to the image transmission apparatus 98 in the remote support system room 76, which is shown in FIG. 10, via signal isolating means.

To be more specific, the image transmission apparatus 98 is connected to the third monitor 104 and indoor camera 105 via video transformers 112 and 113. The other components are identical to those of the fourth embodiment. The same reference numerals will be assigned to the components identical to those of the fourth embodiment. The description of the components will be omitted.

Actions made in accordance with the present embodiment are nearly identical to those with the fourth embodiment. For example, if the public line 74 is struck by lightning, the electric equipment connected to the image transmission apparatus 87 in the surgery system 72 are protected from being damaged as they are in the fourth embodiment. Moreover, the possibility that the operator and patient 77 may get an electric shock is reliably eliminated as it is in the fourth embodiment. In addition, the electric equipment connected to the image transmission apparatus 98 in the remote control room 73, or more particularly, the third monitor 104 and indoor camera 105 can be protected from being damaged.

According to the present embodiment, the electric equipment connected to the image transmission apparatus 97 in the surgery system 72 can be protected from being damaged. The possibility that the operator and patient 77 may get an electric shock can be eliminated reliably. Besides, the electric equipment connected to the image transmission apparatus 98 in the remote support system 73 can be protected from being damaged.

Moreover, even when the remotely supporting operator 106 handles the electric equipment connected to the image transmission apparatus 93, the possibility that the remotely supporting operator 106 may get an electric shock can be eliminated reliably.

Figure 12:
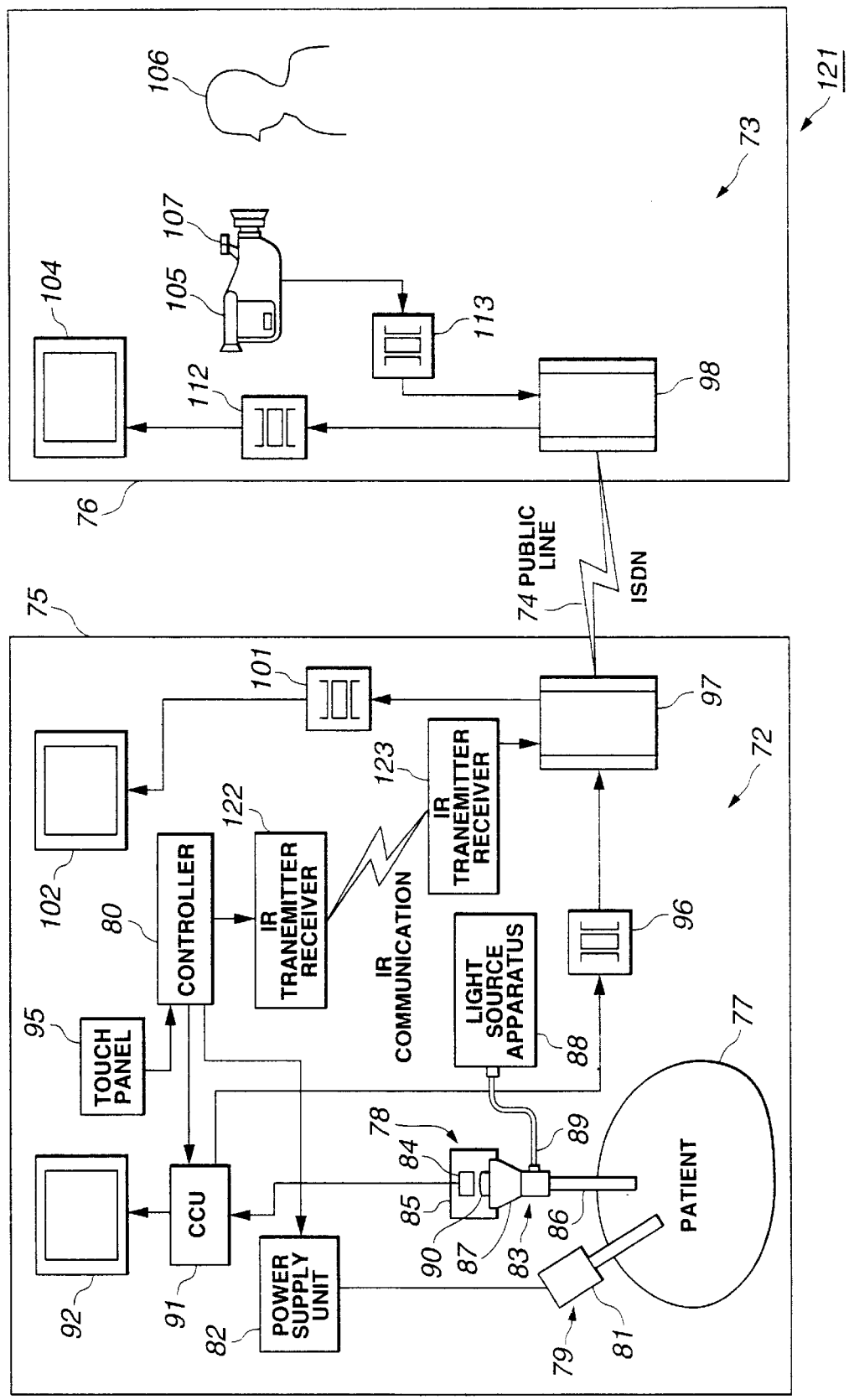
FIG. 12 shows the overall configuration of a remote surgery support system in accordance with the sixth embodiment of the present invention.

Next, the sixth embodiment of the present invention will be described with reference to FIG. 12. FIG. 12 shows the configuration of a remote surgery support system 121 in accordance with the sixth embodiment of the present invention.

Instead of connecting the controller 80 and the image transmission apparatus 97 via the optical modems 99 as shown in FIG. 10, the remote surgery support system 121 has the controller 80 connected to an (first) infrared transmitter receiver (IR transmitter receiver in FIG. 12) 122. Moreover, the image transmission apparatus 97 is connected to a second infrared transmitter receiver 123. The first and second infrared transmitter receivers 122 and 123 communicate with each other in a wireless state using infrared light. Thus, image information or the like can be communicated with the electrical isolation between the controller 80 and image transmission apparatus 97 maintained.

The other components are identical to those of the fifth embodiment.

Next, operations to be exerted by the present embodiment will be described. The present embodiment is different from the fifth embodiment in terms of an operation to be exerted by a unit for transmitting a control signal or the like sent from the controller 80 to the image transmission apparatus 98. The unit will be described below.

An electric signal such as a control signal sent from the controller 80 is converted into an infrared signal by the infrared transmitter receiver 122, and transferred to the infrared transmitter receiver 123. The infrared transmitter receiver 123 receives the infrared signal, converts it into an electric signal, and supplies the electric signal to the image transmission apparatus 97. The image transmission apparatus 97 transmits the signal to the image transmission apparatus 98 over the public line 74. The image transmission apparatus 98 outputs the signal to the third monitor 104 via the connected video transformer 112. The signal is then superimposed on a video signal expressing endoscopic images and being sent from the CCU 91.

If the public line 74 is struck by lightning, almost the same operation as that exerted by the fifth embodiment is expected. Namely, the electric equipment connected to the image transmission apparatus 97 in the surgery system 72 can be protected from being damaged, and the possibility that the operator and patient 77 may get an electric shock can be eliminated reliably. Besides, the electric equipment connected to the image transmission apparatus 98 in the remote support system 73 can be protected from being damaged.

According to the present embodiment, the controller 80 and image transmission apparatus 97 communicate with each other in a wireless state using infrared light. Alternatively, the infrared communication means may be substituted for the video transformer 86 or 101 connected between the image transmission apparatus 97 and CCU 91 or between the image transmission apparatus 97 and second monitor 102.

The present embodiment has nearly the same advantages as the fifth embodiment. Namely, the electric equipment connected to the image transmission apparatus 97 in the surgery system 72 can be protected from being damaged, and the possibility that the operator and patient 77 may get an electric shock can be eliminated reliably. Besides, the electric equipment connected to the image transmission apparatus 98 in the remote support system 73 can be protected from being damaged.

Moreover, even when the remotely supporting operator 106 handles the electric equipment connected to the image transmission apparatus 98, the possibility that the remotely supporting operator 106 gets an electric shock can be eliminated reliably.

Incidentally, an apparatus designed for infrared wireless communication may be substituted for the video transformer 112 or 113 in the remote room 76.

Figure 13:
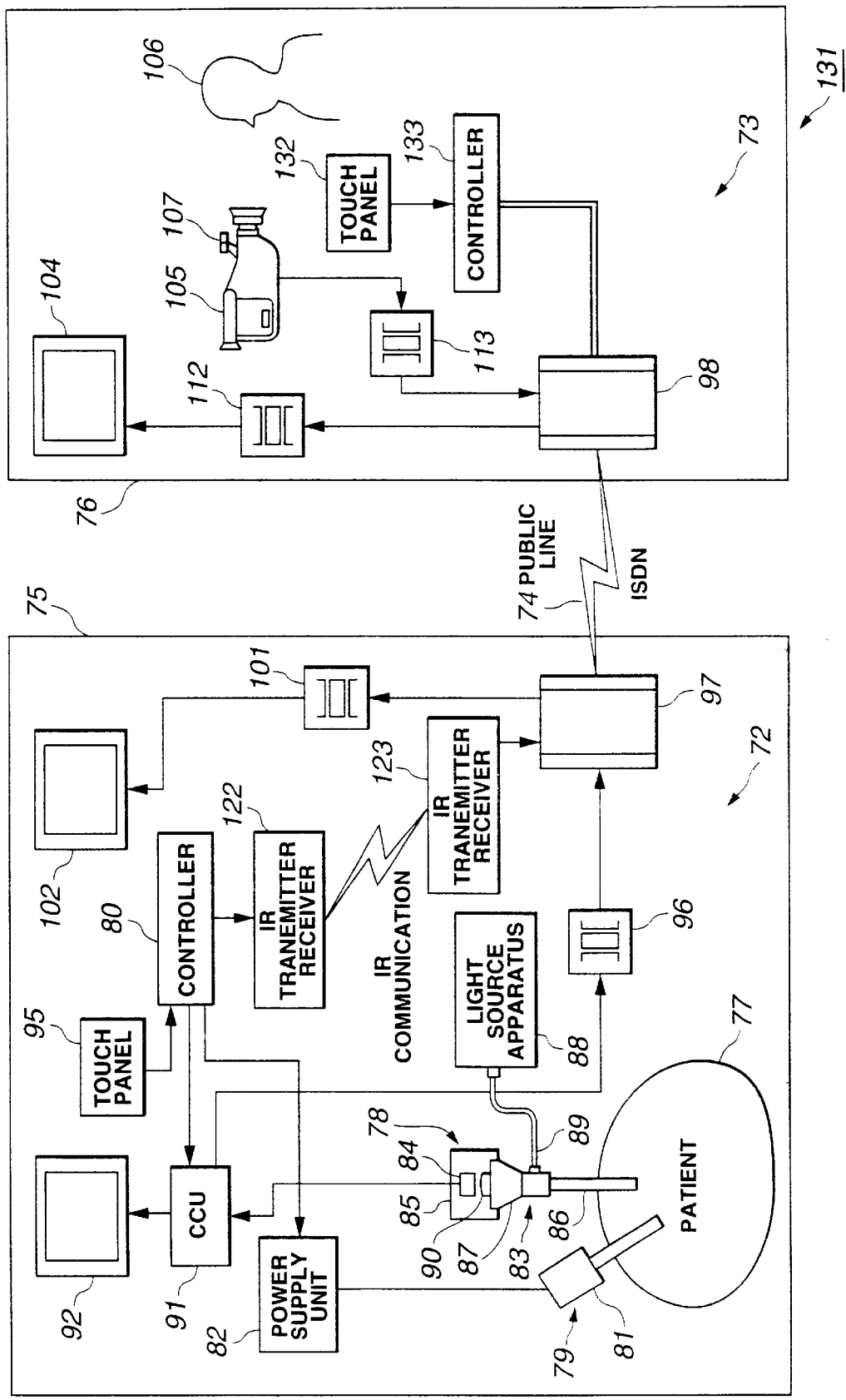
FIG. 13 shows the overall configuration of a remote surgery support system in accordance with the seventh embodiment of the present invention.

Next, the seventh embodiment of the present invention will be described with reference to FIG. 13. FIG. 13 shows the configuration of a remote surgery support system 131 in accordance with the seventh embodiment of the present invention.

According to the present embodiment, the remotely supporting operator 106 in the remote room 76 shown in FIG. 12 can operate the controller 94 in the operating room 75 so as to send a control signal used to control the surgical instrument 79. Specifically, a touch panel 132 (or a keyboard) is included as an input means, and a controller 133 is included for producing a control signal according to an entry made by manipulating the touch panel 132. The controller 133 is connected to the image transmission apparatus 98 via optical modems 134 serving as signal isolating means. The other components are identical to those of the sixth embodiment.

One of operations to be exerted by the present embodiment is such that the remotely supporting operator 106 can control the surgical instrument 79 or can set parameter values for the surgical instrument 79. In other words, depending on the contents of surgery, the remotely supporting operator 106 may be able to set more appropriate parameter values including an output value of electric energy supplied to, for example, an electric cautery used for resection. The present embodiment would prove useful in this kind of case.

The other operations are nearly identical to those of a the sixth embodiment.

The present embodiment has nearly the same advantages as the sixth embodiment.

Incidentally, the wireless communication means is not limited to the infrared communication means but may be wireless communication means using a high-frequency electromagnetic wave or the like.

The controller 133 in the remote room 76 has the ability to transmit a control signal, which is produced according to an entry made at the touch panel 132, to the operating room 75 via the optical modems 134 and image transmission apparatus 98. Furthermore, a video signal of endoscopic images or a control signal transmitted from the CCU 91 or controller 80 in the operating room 75 may be able to be input to the controller 133 via the image transmission apparatus 98 and optical modems 134. A video capture control unit for capturing a video signal or an I/O interface included in the controller 133 captures the video signal. The position of a region to be resected during surgery may then be marked in images expressed by the video signal. The video signal may then be returned to the operating room.

Moreover, a display device such as a monitor may be connected to the controller 133 so that images captured by the video capture control unit in the controller 133 or information indicated with a control signal can be displayed as an overlay.

Moreover, a communication line linking the operating room and remote room may be, aside from the public line 74, a local area network (LAN) or a wide area network (WAN).

Next, a medical information processing system will be described with reference to FIG. 14 to FIG. 18. The medical information processing system is intended to improve the efficiency in retrieving medical information including a plurality of different kinds of image data that have relation to one another so as to thus improve the efficiency in working on information at a medical institute or the like.

Figure 14:
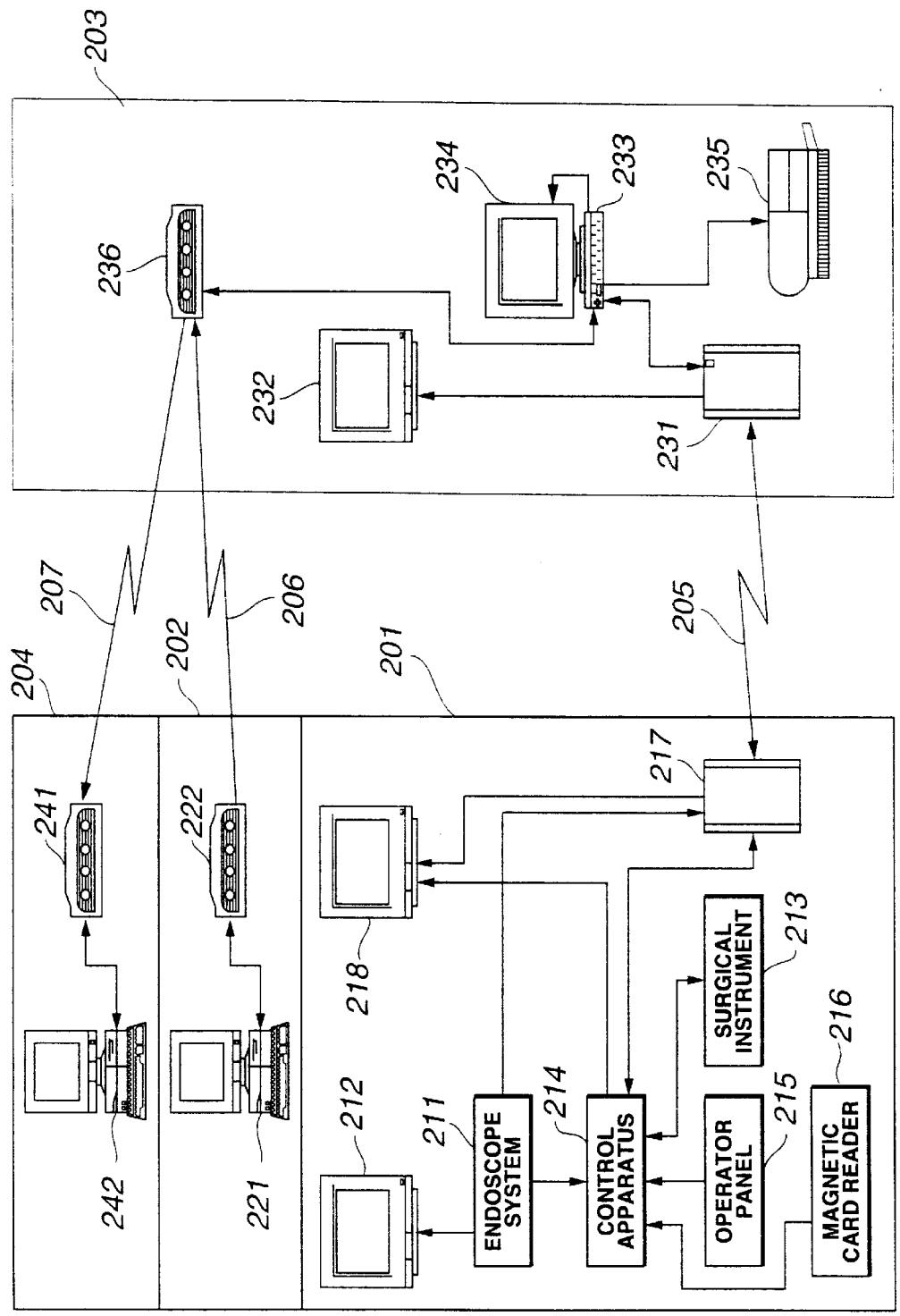
FIG. 14 to FIG. 18 relate to the eighth embodiment of the present invention.

As shown in FIG. 14, a medical information processing system consists mainly of an operating room system 201, a plurality of examination room systems 202, an information accumulation system 203, and an information reference apparatus 204. The operating room system 201 is installed in an operating room or any other site and acquires endoscopic image data, surgery system information, and patient information. The examination room apparatuses 202 are installed in examination rooms dedicated to examinations performed using an MRI system, a CT scanner, a diagnostic ultrasound system, and an X-ray system respectively, and acquire a plurality of kinds of image data different from endoscopic image data. The information accumulation system 203 is installed in a site other than the operating room and examination rooms, accumulates various kinds of image data acquired by the operating room system 201 and examination room systems 202 and non-image data, and produces clinical recordings. The information reference apparatus 204 is used to reference medical information accumulated in the information accumulation system 203. The operating room system 201 and information accumulation system 203, the examination room systems 202 and information accumulation system 203, and the information reference apparatus 204 and information accumulation system 203 are linked by public lines or any other communication lines 205, 206, and 207 respectively.

The operating room system 201 consists mainly of an endoscope system 211, a display device 212, a surgical apparatus 213, a control apparatus 214, a manipulating means such as an operator panel 215, a patient information input means such as a magnetic card reader 216, a signal transmission apparatus 217, and a display device 218. The endoscope system 211 images a region to be examined in a patient's body cavity and acquires endoscopic image data. The display device 212 displays endoscopic images produced by the endoscope system 211. The surgical apparatus 213 is, for example, an electric cautery, a pneumoperitoneum unit, or an ultrasonic surgical apparatus. The control apparatus 214 has the ability to acquire surgical apparatus information such as information of measures provided by the surgical apparatus 213. The operator panel 215 is connected to the control apparatus 214 and used to input a control instruction or the like, according to which the surgical apparatus 213 should be controlled, to the control apparatus 214. The magnetic card reader 216 reads patient information from a magnetic card and supplies it to the control apparatus 214. The signal transmission apparatus 217 transmits endoscopic image data, surgical apparatus information, and patient information to the information accumulation system 203 installed in another site over a communication line 205, and communicates with the information accumulation system 203 so as to receive data. The display device 218 displays surgical apparatus information and patient information supplied from the control apparatus 214 and also displays information contained in data received from the other sites via the signal transmission apparatus 217.

The examination room systems 202 include examination systems that are not shown, image filing apparatuses 221, and a communicating means such as a modem 222. The examination systems include an MRI system, a CT scanner, a diagnostic ultrasound system, and an X-ray system. The image filing apparatuses 221 accumulate image data acquired by the examination systems. The modem 222 connects the image filing apparatuses 221 to the other sites over communication lines 6. The image data accumulated in the image filing apparatuses 221 can be transmitted to the other sites. The image data stored in the image filing apparatuses 221 may not be solely image data but may contain non-image data such as data associated with the image data, for example, findings.

The information accumulation system 203 consists mainly of a signal transmission apparatus 231, a display device 232, an information accumulation apparatus 233, a display device 234, a printer 235, and a communicating means such as a modem 236. The signal transmission apparatus 231 communicates with the signal transmission apparatus 217. The display device 232 displays endoscopic image data, surgical apparatus information, and patient information received from the other sites via the signal transmission apparatus 231. The information accumulation apparatus 233 accumulates medical information such as the endoscopic image data, surgical apparatus information, and patient information received from the other sites via the signal transmission apparatus 231, and image data other than the endoscopic image data. The information accumulation apparatus also edits the medical information. The display device 234 displays the medical information accumulated in the information accumulation apparatus 233. The printer 235 prints clinical recordings produced by editing the medical information accumulated in the information accumulation apparatus 233. The modem 236 enables transfer of the medical information between the examination room systems 2 or information reference apparatus 204 and the information accumulation apparatus 233.

The information reference apparatus 204 consists of a communicating means such as a modem 241 and a terminal unit 242. The modem 241 enables transfer of medical information to or from the other sites. The terminal unit 242 is used to reference the medical information accumulated in the information accumulation system 203 via the modem 241. The terminal unit 242 may be designed, if necessary, to be able to edit the medical information accumulated in the information accumulation system 203.

Figure 15:
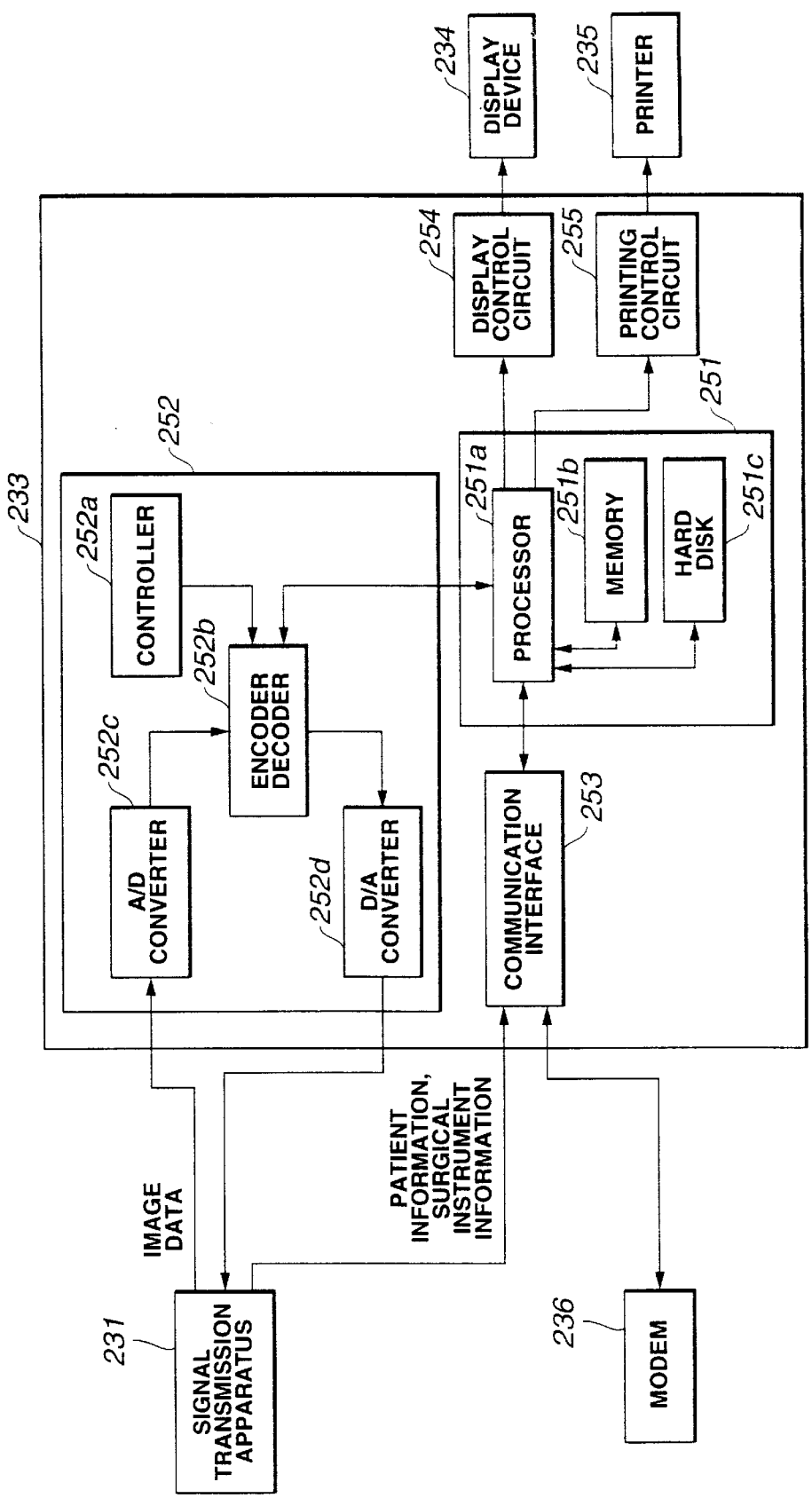

As shown in FIG. 15, the information accumulation apparatus 233 consists mainly of a control circuit 251, a video signal input/output circuit 252, a communication interface 253, a display control circuit 254, and a printing control circuit 255. The control circuit 251 controls the components of the information accumulation apparatus 233. The video signal input/output circuit 252 inputs or outputs endoscopic image data from or to the signal transmission apparatus 231. The communication interface 253 enables input or output of medical information between the signal transmission apparatus 231 and modem 236. The display control circuit 254 is controlled by the control circuit 251 and outputs a video signal used to drive the display device 234. The printing control circuit 255 is controlled by the control circuit 251 and outputs a video signal used to drive the printer 235.

The control circuit 251 has such hardware devices as a processor 251a, a memory 251b, and a hard disk 251c. The processor 251a is operated by software. Software programs to be run by the processor 251a and medical information are stored in the memory 251b and hard disk 251c. A work area to be used by the processor 251a is preserved in the memory 251b.

The video signal input/output circuit 252 consists of a controller 252a, an encoder decoder 252b, an A/D converter 252c, and a D/A converter 252b. The controller 252a controls the circuit elements of the video signal input/output circuit 252. The encoder decoder 252b encodes or decodes image data. The A/D converter 252c converts input image data from an analog form to a digital form. The D/A converter 252b converts the image data from the digital form to the analog form and outputs resultant digital data.

Figure 16:
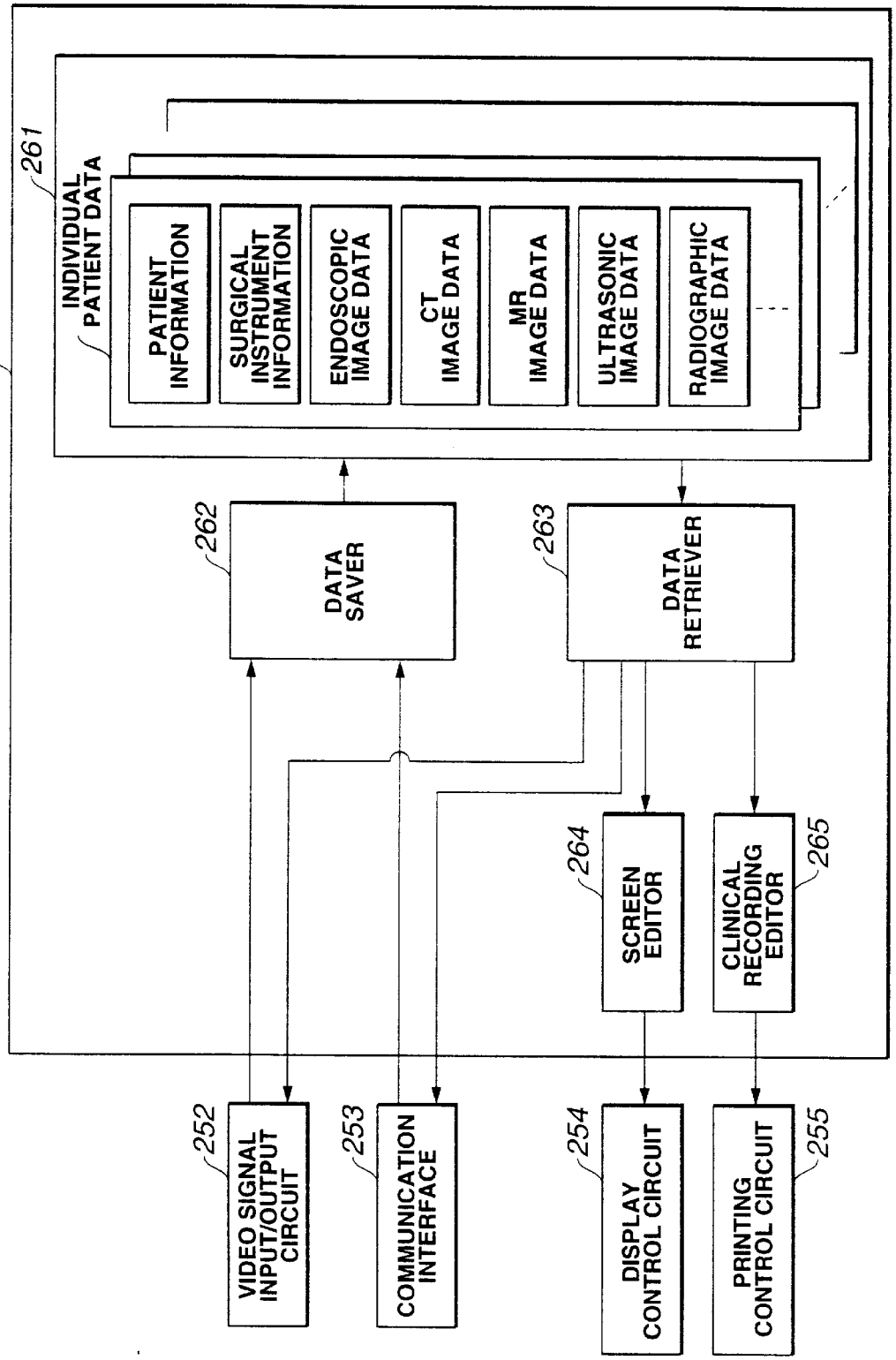

As shown in FIG. 16, the control circuit 251 has such functional elements as a data memory 261, a data saver 262, a data retriever 263, a screen editor 264, and a clinical recording editor 265. The data memory 261 is used to store data. The data saver 262 saves data, which is input via the video signal input/output circuit 252 and communication interface 253, in the data memory 261. The data retriever 263 retrieves and reads data from the data memory 261. The screen editor 264 edits data read by the data retriever 263 according to a screen display format. The clinical recording editor 265 edits data read by the data retriever 263 according to a printout format of clinical recordings.

Figure 17:
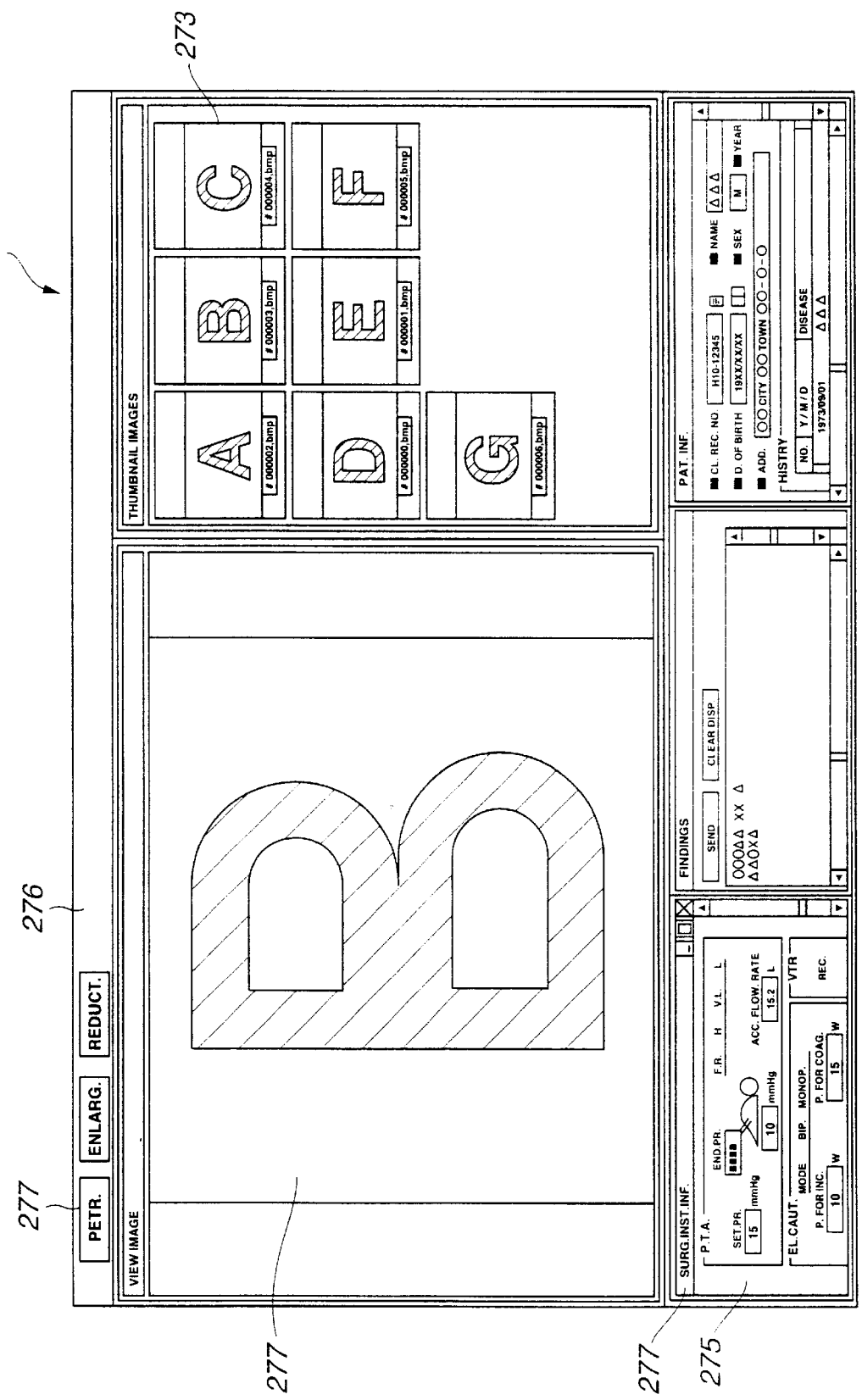

As shown in FIG. 17, a medical information display screen 271 visualized with the display device 234 by means of the information accumulation apparatus 233 consists of a view image area 272, a thumbnail image area 273, a patient information area 274, a surgical apparatus information area 275, and an operation menu display area 276. View images including endoscopic images are displayed in the view image area 272. A plurality of thumbnail images produced by reducing image data, for example, thinning pixels constituting image data is displayed in the thumbnail image area 273. Patient information is displayed in the patient information area 274. Surgical apparatus information is displayed in the surgical apparatus information area 275. The operation menu display area 276 is used to execute such an operation as retrieval of medical information or display of images. A button 277 used to activate the facility for performing the operation of retrieval of medical information, and other buttons are arranged in the operation menu display area 276.

What are referred to as the buttons are areas in the screen to which facilities are allocated. When any of the buttons is selected using a mouse or the like that is not shown, an allocated facility is activated.

Figure 18:
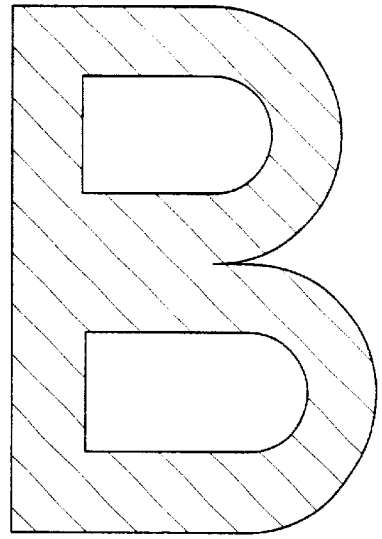

As shown in FIG. 18, a clinical recording printout 281 output from the printer 235 driven by the information accumulation apparatus 233 has a view image area 282, a thumbnail image area 283, and a patient information area 284 arranged therein.

Next, operations to be exerted by the present embodiment will be described below.

Prior to surgery, a magnetic card in which patient information is stored is inserted into the magnetic card reader 216. The patient information read by the magnetic card reader 216 is supplied to the control apparatus 214. When surgery starts, the endoscope system 211 and surgical apparatus 213 are employed.

The endoscope system 211 is used to image a region to be observed in a patient's body cavity. A video signal containing endoscopic image data and being produced by the endoscope system 211 is output to the display device 212. Endoscopic images are then displayed on the display device 212. At this time, the operator panel 215 may be manipulated in order to control the endoscope system 211, that is, to adjust the tone of the endoscopic images. The control apparatus 214 controls the endoscope system 211 according to the manipulation.

The operator panel 215 may be manipulated in order to control the surgical apparatus 213. The control apparatus 214 then controls the surgical apparatus 213 according to the manipulation. When it says that the surgical apparatus 213 is controlled, it means that power output to the electric cautery or pressure applied to an abdominal cavity by a pneumoperitoneum unit is set to a certain level. Moreover, information of measures provided by the surgical apparatus 213 is given to the control apparatus 214. The measure information is information of a measure of, for example, pressure actually applied to a patient abdominal cavity by the pneumoperitoneum unit. Thus, the patient information sent from the control apparatus 214 and surgical apparatus information are displayed on the display device 18. The surgical apparatus information contains information of the set state of the endoscope system 211, information of the set state of the surgical apparatus 213, and the measure information provided by the surgical apparatus 213.

Endoscopic image data produced by the endoscope system 211, and patient information and surgical apparatus information sent from the control apparatus 214 are supplied to the signal transmission apparatus 231 included in the information accumulation system 203 over the communication line 205. The signal transmission apparatus 231 transfers the input endoscopic image data, patient information, and surgical apparatus information to the display device 232 connected to the signal transmission apparatus 231, and also transfers them to the information accumulation apparatus 233. For transmitting image data, if necessary, the signal transmission apparatus 217 encodes or decodes the image data.

MR image data, CT image data, ultrasonic image data, and radiographic image data acquired in the respective examination rooms are accumulated in the image filing apparatuses 221 installed in the examination rooms. The image data accumulated in the image filing apparatuses 221 are transmitted to the information accumulation apparatus 233 by way of the modems 222, communication lines 206, and modem 236.

As mentioned above, medical information composed of endoscopic image data, patient information, surgical apparatus information, and various kinds of image data other than the endoscopic image data is transmitted to the information accumulation apparatus 233 via the signal transmission apparatus 231 and modem 236 serving as communicating means. The endoscopic image data sent to the information accumulation apparatus 233 via the signal transmission apparatus 231 is transferred to the video signal input/output circuit 252. The endoscopic image data is converted into digital data or, if necessary, decoded, and then applied to the control circuit 251.

The patient information, surgical apparatus information, and various kinds of image data sent to the information accumulation apparatus 233 via the signal transmission apparatus 231 and modem 236 are transferred to the control circuit 251 via the communication interface 253.

The medical information transferred to the control circuit 251 is saved in the data memory 261 by the data saver 262. At this time, the data saver 262 associates mutually relevant medical information with one another, for example, sorts medical information by patient name and then saves it in the data memory 261. For sorting medical information and saving it in the data memory 261, for example, mutually relevant medical information may be integrated into one file.

For retrieving desired medical information from the data memory 261, for example, the button 277 in the operation menu display area 276 in the medical information display screen 271 is pointed out using a mouse or the like that is not shown. A screen for prompting press of keys relevant to retrieval, which is not shown, then appears. The keys relevant to retrieval are then pressed with the screen displayed. This causes the data retriever 263 to retrieve and read medical information designated with the pressed keys from the data memory 261.

For example, assume that a patient name, a patient code, or the like for identifying a patient is keyed in. Medical information concerning the designated patient is then read from the data memory 261. At this time, image data out of the medical information may be, if necessary, converted into thumbnail image data expressing reduced images, and then output.

The screen editor 264 edits medical information retrieved by the data retriever 263 according to a screen display format. The resultant medical information is displayed on the display device 234 via the display control circuit 254 with respective information items allocated to the display areas of the medical information display screen 271. At this time, for example, thumbnail images produced by reducing in size image data are displayed in the thumbnail image area 273. Surgical apparatus information is displayed in the surgical apparatus information area 275, and patient information is displayed in the patient information area 274.

In the thumbnail image area 273, not only endoscopic images but also various kinds of images other than the endoscopic images are displayed. When any of one or more thumbnail images displayed in the thumbnail image area 273 is designated using a mouse or the like that is not shown, an image that is not thumbnail but associated with the designated thumbnail image appears in the view image area 272. In the view image area 272, not only an endoscopic image but also any of the other various kinds of images can be displayed if necessary.

The clinical recording editor 265 edits medical information retrieved by the data retriever 263 according to a clinical recording printout format. The resultant medical information is then supplied to the printing control circuit 255. Consequently, the printer 235 provides the clinical recording printout 281.

Medical information retrieved by the data retriever 263 is also output to the display device 218 by way of the video signal input/output circuit 252, communication interface 253, signal transmission apparatus 231, communication line 205, and signal transmission apparatus 217. At this time, image data output from the control circuit 251 is, if necessary, encoded by the video signal input/output circuit 252, converted into analog data, and then transmitted to the signal transmission apparatus 231.

In response to a request for retrieval of medical information, the data retriever 263 retrieves and reads designated medical data from the data memory 261 by way of the terminal unit 242, modem 241, communication line 207, modem 236, and communication interface 253. The medical data is then transmitted to the terminal unit 242.

For example, the information accumulation system 203 may be used as, for example, the remote support system 6 included in the first embodiment to support surgery.

An operator of the information accumulation system 203 displays endoscopic image data and patient data, which are sent from the operating room system 201, on the display device 232 so as to monitor the progress of surgery. Moreover, information relevant to the surgery is displayed on the display device 234. According to the first embodiment, data stored in the remote support system 6 is utilized as information relevant to surgery. According to the present embodiment, any information can be fetched from the examination room systems 202 or the like.

Information useful in supporting an operator, such as, images representing what must be noted for surgery is output to the display device 218 via the signal transmission apparatus 231 and the signal transmission apparatus 217 in the operating room system 201.

As described above, according to the present embodiment, medical information including a plurality of different kinds of image data and being correlated is stored while being associated with one another. The medical information including the plurality of different kinds of image data and being correlated can be retrieved easily.

According to the present embodiment, the efficiency in retrieving medical information including a plurality of different kinds of image data and being correlated improves. This exerts the effect that the efficiency in working on information at a medical institution improves.

The present embodiment is not limited to the aforesaid mode. Various variants of the present embodiment can be made without a departure from the gist of the present invention.

Specifically, the communication lines 205, 206, and 207 are not limited to public lines but may be leased lines, local area networks (LAN), or any other communication lines. Moreover, the information reference apparatus 204 may be installed in the same site as the operating room system 201 or the examination room systems 202. The examination room systems 202 may be installed in the same site as the operating room system 201 or the information accumulation system 203.

According to the present embodiment, an input means for inputting patient information is realized with the magnetic card reader 216. However, the input means is not limited to the magnetic card reader. Alternatively, an apparatus for reading patient information from an IC card, an optical card, or any other medium other than the magnetic card will do.

Moreover, the image filing apparatus 221 may be realized with a computer having a display facility.

Moreover, the terminal unit 242 may be realized with a computer having a display facility.

Moreover, the information accumulation apparatus 233 may have the ability to display medical information read from the data memory 261 as well as medical information fetched, if necessary, by way of the signal transmission apparatus 231 and modem 236 on the medical information display screen 271 instead of accumulating the medical information.

The modems 222, 236, and 241 may be replaced with any other communicating means, for example, terminal adaptors or routers.

Retrieval-related keys to be pressed for retrieving medical information from the data memory 261 are not limited to keys identifying a patient but may be any other keys. For example, keys indicating a date of surgery, keys identifying an operator, or keys identifying a kind of case will do. Otherwise, a plurality of sets of keys may be used in combination. Medical information is stored in the data memory 216 while being associated with one another according to the set of keys to be employed.

According to the present embodiment, image data is transmitted from a remote site to the information accumulation system over a communication line. The present embodiment is not limited to this mode. Alternatively, a portable magneto-optical disk or the like on which image data is stored may be transported from a remote site to the information accumulation system, and image data may be saved from the recording medium to the information accumulation apparatus.

Next, a medical information processing system facilitating the efficiency in producing clinical recordings by saving the time required for acquiring and accumulating medical treatment information will be described with reference to FIG. 19 to FIG. 22.

Figure 19:
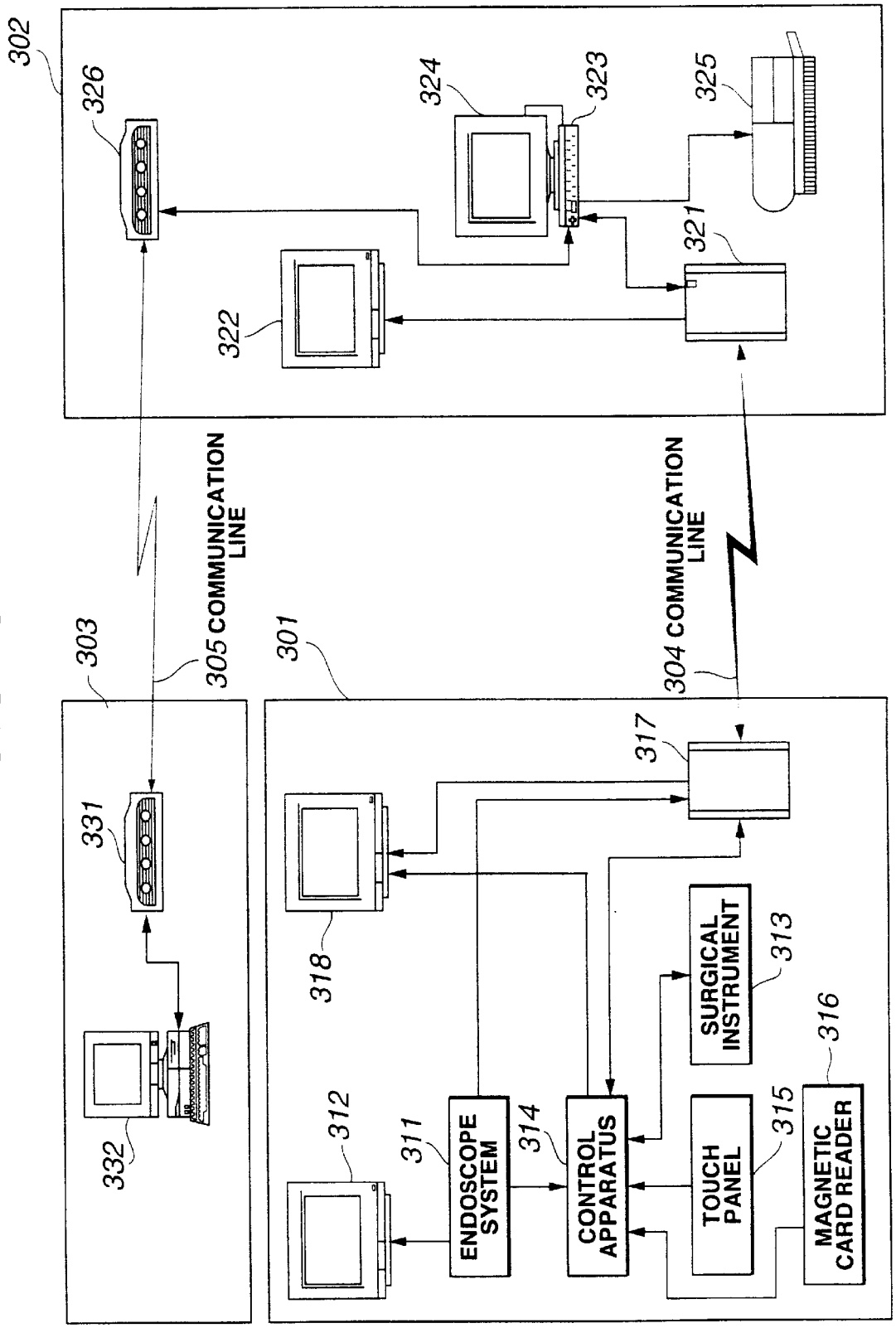
FIG. 19 to FIG. 22 relate to the ninth embodiment of the present invention.

As shown in FIG. 19, a medical information processing system of the present embodiment consists mainly of an operating room system 301, an information accumulation system 302, and an information reference apparatus 303. The operating room system 301 is installed in an operating room or any other site, and acquires various kinds of medical information in the operating room or the like. The information accumulation system 302 is installed remotely from the operating room 301, accumulates various kinds of medical treatment information acquired by the operating room system 301, and producing clinical recordings. The information reference apparatus 303 is installed in a site different from the site in which the information accumulation system 302 is installed, and used to reference clinical recording information produced by the information accumulation system 302. The operating room system 301 and information accumulation system 302 and the information accumulation system 302 and information reference apparatus 303 are linked by communication lines 304 and 305 respectively.

The communication lines 304 and 305 may be public lines, leased lines, local area networks (LAN), or any other communication lines. The information reference apparatus 303 may be installed in the same site as the operating room system 301.

The operating room system 301 consists mainly of an endoscope system 311, a display device 312, a surgical apparatus 313, a control apparatus 314, a surgical apparatus control input means such as a touch panel 315, a patient information input means such as a magnetic card reader 316, a signal transmission apparatus 317, and a display device 318. The endoscope system 311 images a region to be examined such as a patient's intracavitary region and produces a video signal containing endoscopic image data. The display device 312 visualizes a video signal produced by the endoscope system 311. The surgical apparatus 313 is, for example, an electric cautery, a pneumoperitoneum unit, or an ultrasonic surgical apparatus. The control apparatus 314 controls the surgical apparatus 313 and produces surgical apparatus information including information of measures supplied from the surgical apparatus 313. The touch panel 315 is connected to the control apparatus 314 and used to enter a control instruction or the like, according to which the surgical apparatus 313 is controlled, to the control apparatus 314. The magnetic card reader 316 reads patient information from a magnetic card and supplies it to the control apparatus 314. The signal transmission apparatus 317 transmits a video signal, surgical apparatus information, and patient information to the information accumulation system 302 located in another site over a communication line, and communicates with the information accumulation system 302 so as to receive information therefrom. The video signal contains endoscopic image data produced by the endoscope system 311, and the surgical apparatus information is supplied from the control apparatus 314. The display device 318 displays the surgical apparatus information and patient information supplied from the control apparatus 314 or information received from another site by the signal transmission apparatus 317.

The information accumulation system 302 consists mainly of a signal transmission apparatus 321, a display device 322, a control apparatus 323, a display device 324, a printer 325, and a communicating means such as a modem 326. The signal transmission apparatus 321 communicates with the signal transmission apparatus 317. The display device 322 displays endoscopic image information, surgical apparatus information, and patient information received from another site via the signal transmission apparatus 321. The control apparatus 323 accumulates medical treatment information including the endoscopic image information, surgical apparatus information, and patient information received from another site via the signal transmission apparatus 321, and produces a video signal expressing a screen into which the images and information are integrated. The control apparatus 323 also has the ability to integrate the information and edit it so as to produce a clinical recording, and to output the clinical recording to the printer. The display device 324 displays the information integrated by the control apparatus 323. The printer 325 prints out the clinical recording produced by the control apparatus 323. The modem 326 helps transmit the information, which is integrated by the control apparatus 323, to the information reference apparatus 303 in another site over the communication line 305.

The information reference apparatus 303 consists mainly of a communicating means such as a modem 331 and a terminal unit 332. The modem 331 communicates with the communicating means such as the modem 326, and the terminal unit 332 communicates with the control apparatus 323 via the modem 331 so as to reference information integrated by the control apparatus 323 or input or edit information.

Figure 20:
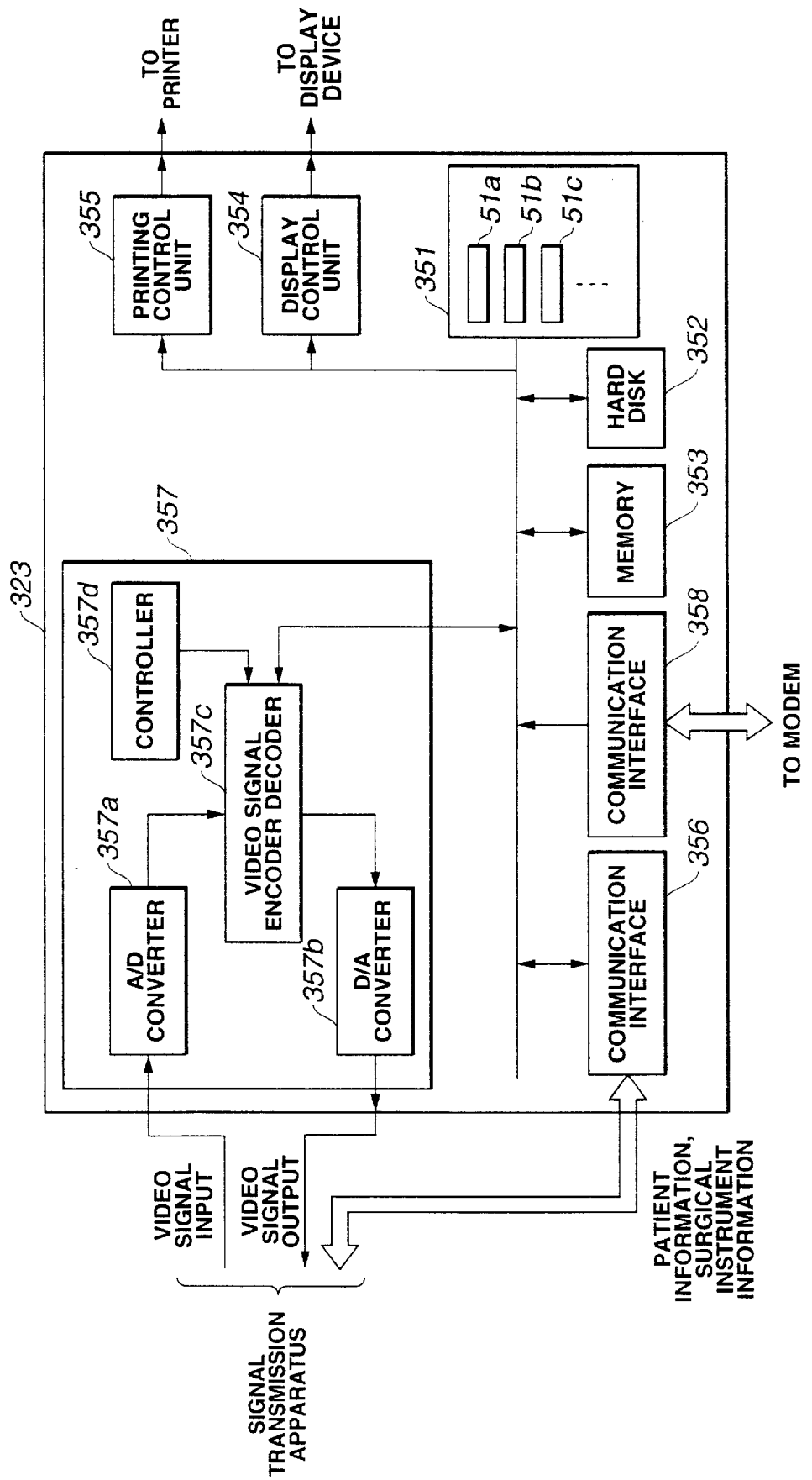

As shown in FIG. 20, the control apparatus 323 consists mainly of a processor 351, a hard disk 352, a memory 353, a display control unit 354, a printing control unit 355, a communication interface 356, a video signal input/output circuit 357, and a communication interface 358. The processor 351 controls the components of the control apparatus 323. Software programs to be run by the processor 351 and data such as the endoscopic images and patient information are stored in the hard disk 352 and memory 353. Besides, a work area used by the processor 351 is preserved in the memory 353. The display control unit 354 produces a video signal used to drive the display device 324. The printing control unit 355 produces a video signal used to drive the printer 325. The communication interface 356 helps transmit the patient information and surgical apparatus information to or from the signal transmission apparatus 321. The video signal input/output circuit 357 inputs or outputs video information including endoscopic image data from or to the signal transmission apparatus 321. The communication interface 358 transmits information to the modem 326.

The processor 351 consists mainly of an information accumulation unit 351a, a display information production unit 351b, and a clinical recording production unit 351c. The endoscopic image data, patient information, and surgical apparatus information, which are input independently via the signal transmission apparatus 321, are accumulated in the information accumulation unit 351a together with the software programs stored in the hard disk 352 and memory 353. The display information production unit 351b edits information accumulated in the information accumulation unit 351a, and produces screen information concerning a screen display on the display device 324. The clinical recording production unit 351c edits the accumulated information and produces a clinical recording to be output to the printer 325.

The video signal input/output circuit 357 consists mainly of an A/D converter 357a, a D/A converter 357b, a video signal encoder decoder 357c, and a controller 357d. The A/D converter 357a converts an input analog video signal into a digital video signal. The D/A converter 357b converts a digital video signal into an analog video signal and outputs the analog video signal. The video signal encoder decoder 357c decodes a video signal input via the A/D converter 357a, samples a desired endoscopic image signal from the input video signal, encodes a video signal to be output, and supplies the resultant signal to the D/A converter 357b. The controller 357d controls the video signal encoder and decoder 357c and other elements of the video signal input/output circuit 357.

Figure 21:
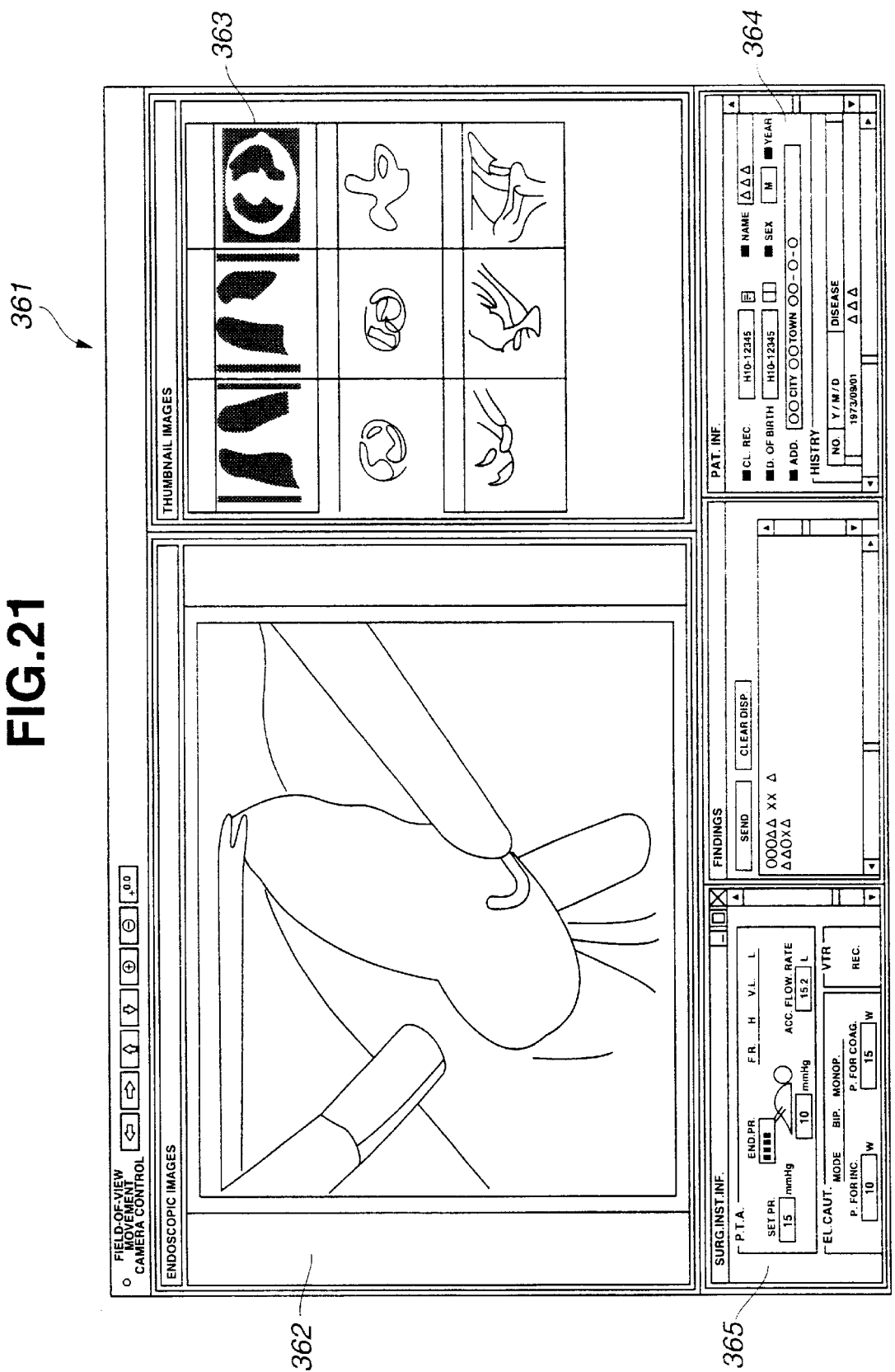

As shown in FIG. 21, an endoscopic image area 362, a thumbnail image area 363, and a surgical apparatus information area 365 are defined in an integrated information screen 361 (displayed on the display device 324 according to an output from the control apparatus 323). Endoscopic images are displayed in the endoscopic image area 362. A plurality of thumbnail images that are reduced images produced by thinning pixels that constitute endoscopic image data is displayed in the thumbnail image area 363. Patient information is displayed in the patient information area 364. Surgical apparatus information is displayed in the surgical apparatus information area 365.

Figure 22:
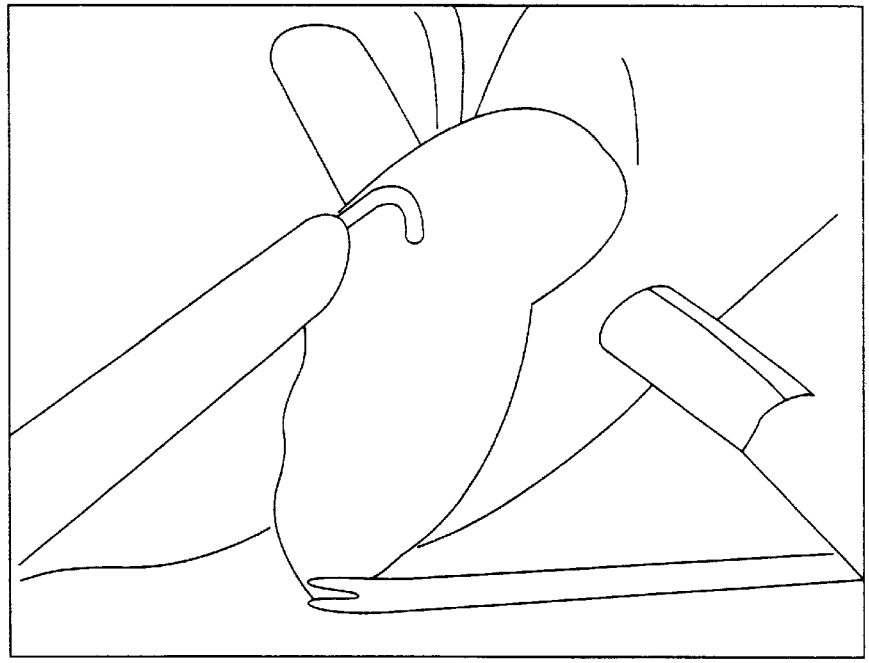

As show in FIG. 22, an endoscopic image area 372, a thumbnail image area 373, and a patient information area 374 are defined in a clinical recording 371 (output from the printer 325 according to an output from the control apparatus 323).

Next, operations to be exerted by the present embodiment will be described below.

A video signal containing endoscopic image data produced by the endoscope system 311 during endoscopic examination is transmitted to the signal transmission apparatus 317. The signal transmission apparatus 317 encodes a video signal and transmits it to the signal transmission apparatus 321 over the communication line 304. The video signal received by the signal transmission apparatus 321 is converted into a digital signal by the A/D converter 357a in the video signal input/output circuit 357 included in the control apparatus 323, and then decoded by the video signal encoder decoder 357c.

At this time, if necessary, the video signal encoder decoder 357c samples desired endoscopic image data contained in the video signal under the control of the control unit 357d controlled by the processor 351. The endoscopic image data fetched by the video signal input/output circuit 357 is accumulated in the information accumulation unit 351a.

Surgical apparatus information sent from the touch panel 315 and surgical apparatus 313 to the control apparatus 314 is fed to the signal transmission apparatus 317. The signal transmission apparatus 317 transmits the surgical apparatus information to the signal transmission apparatus 21 over the communication line 4. The surgical apparatus information received by the signal transmission apparatus 321 is fetched into the control apparatus 323 via the communication interface 356 and accumulated in the information accumulation unit 351a.

On the other hand, patient information supplied from the magnetic card reader 316 to the control apparatus 314 is fed to the signal transmission apparatus 317. The signal transmission apparatus 317 transmits the patient information to the signal transmission apparatus 321 over the communication line 304. The patient information received by the signal transmission apparatus 321 is fetched into the control apparatus 323 via the communication interface 356 and accumulated in the information accumulation unit 351a.

As mentioned above, information such as endoscopic image information, surgical apparatus information, and patient information input from different apparatuses or arisen on different occasions are accumulated in the information accumulation unit 351a in the control apparatus 323.

Information accumulation in the information accumulation unit 351a is edited based on a screen display format by the display information production unit 351b, whereby the integrated information screen 361 is displayed on the display device 325. Endoscopic image information, patient information, and surgical apparatus information input from different input units or arisen on different occasions are integrated into the integrated information screen 361. In the integrated information screen 361, if any thumbnail image is selected from among thumbnail images of endoscopic images displayed in the thumbnail image area 363, an endoscopic image associated with the selected thumbnail image may be displayed in the endoscopic image area 362.

Moreover, information accumulated in the information accumulation unit 351a is edited based on a printout format by the clinical recording production unit 351c, whereby the printer 325 outputs a clinical recording 371. Endoscopic image information and patient information input from different input units or arisen on different occasions are integrated into the clinical recording 371.

Information accumulated in the control apparatus 323 is transmitted to the terminal unit 332 in the information reference apparatus 303. At this time, the information is transmitted by way of the modem 326 connected to the communication interface 358, the communication line 305 linked to the modem 326, and the modem 331 included in the information reference apparatus 303. The terminal unit 332 uses, for example, a display device thereof to display information contained in the integrated information screen 361 or clinical recording 371 in an integrated manner. The information reference apparatus 303 may be installed in a plurality of sites. Information accumulated in the information accumulation system 302 may therefore be referenced or, if necessary, edited in any site.

According to the present embodiment, medical treatment information such as endoscopic image information, surgical apparatus information, and patient information that are input from different input units or arise on different occasions are accumulated in the control apparatus 323. The control apparatus 323 causes the display device 324 to display the integrated information screen 361 into which the accumulated information is integrated and which contains clinical recording information. The control apparatus 323 also causes the printer 325 to print out a clinical recording. Consequently, the time required for acquiring and accumulating medical treatment information is reduced, and the efficiency in producing a clinical recording improves.

Moreover, not only endoscopic image information acquired by the endoscope system 311 but also information acquired by related instruments such as various types of surgical instruments 313 can be accumulated.

The magnetic card reader 316 is used to read patient information. The labor for entering patient information at a keyboard or the like is therefore eliminated.

Medical treatment information can be referenced or edited in any site using the information reference apparatus 303.

Medical treatment information acquired by the operating room system 301 installed in an operating room is accumulated in the information accumulation system 302 installed in a remote site, for example, in another room. The medical treatment information can therefore be edited in another room, or tasks related to surgery can be processed to thus provide support from a remote site other than the operating room. In this case, if the information reference apparatus 303 is installed in the operating room, a clinical recording produced with the support provided from the remote site can be referenced in the operating room. Consequently, work can be performed efficiently in the operating room.

The modems 326 and 331 may be replaced with any other communication units, for example, terminal adaptors. The hard disk 352 may be replaced with any other storage means, for example, a magneto-optical disk.

The magnetic card reader 316 may be replaced with an apparatus for reading information from a portable medium other than a magnetic card, such as, an IC card or an optical card.

Various variants of the aforesaid embodiments can be made without a departure from the gist of the present invention.

What is claimed is:

1. A remote surgery support system, comprising:
    a first control means for controlling a surgical instrument used to perform surgery in an operating room;
    an input means for use in inputting information, with which said surgical instrument is controlled, to said first control means;
    a first signal transmission apparatus for receiving information, which indicates the controlled state of said surgical instrument, from said first control means, and converting it into a transmissible signal;
    a communication line over which said transmissible signal produced by first signal transmission apparatus is transmitted from said operating room to a control room in a remote place;
    a second signal transmission apparatus for receiving transmissible signal produced by first signal transmission apparatus over said communication line, and converting it into a signal corresponding to said information;
    a second control means for receiving said signal from said second signal transmission apparatus; and
    a display device for displaying an output of said second control means;
    second input means for use in inputting support information to said second control means; and
    a second display device for inputting said support information from said second control means via said second signal transmission apparatus and said first signal transmission apparatus and displaying the information.

2. A remote surgery support system according to claim 1, further comprising an endoscopic imaging means installed in said operating room for imaging an intracavitary region and controlled by said first control means, wherein a video signal carrying data pertaining to the intracavitary region produced by said endoscopic imaging means is transmitted from said first signal transmission apparatus to said second signal transmission apparatus over said communication line, and
    a signal isolating means for electrically isolating said endoscopic imaging means and/or first control means from said first signal transmission apparatus so as to transmit a signal.

3. A remote surgery support system according to claim 1, further comprising an endoscopic imaging means installed in said operating room for imaging an intracavitary region and producing a video signal, wherein the video signal is transmitted to said second signal transmission apparatus over a communication line to which said first signal transmission apparatus is connected.

4. A remote surgery support system according to claim 3, wherein said video signal transmitted to said second signal transmission apparatus is displayed on a third display device.

5. A remote surgery support system according to claim 3, wherein said video signal transmitted to said second signal transmission apparatus is displayed on said display device using said second control means.

6. A remote surgery support system according to claim 5, wherein said second control means includes a still image capturing means for capturing a still image carried by said video signal.

7. A remote surgery support system according to claim 6, wherein said second control means transmits said support information, which is produced by superimposing information input using said second input means on the captured still image, via said second signal transmission apparatus, and causes said second display device to display said support information.

8. A surgical information display method, comprising the steps of:
    inputting control to be given to a surgical instrument in an operating room to a control means so that surgery can be performed under endoscopic observation;
    transmitting said control to be given to said surgical instrument and endoscopic images produced in said operating room to a remote place via said control means over a communication line; and
    displaying said control to be given to said surgical instrument in said operating room and said endoscopic images on a monitor in the remote place.

9. A surgical information display method according to claim 8, further comprising.
    a step of transmitting support information useful in surgery from said remote place to said operating room over a communication line while viewing said control and said endoscopic image displayed on said monitor, and
    a step of displaying said support information.

10. A surgical information display method, comprising the steps of:
    inputting control to be given to a surgical instrument in an operating room and/or patient information to a control means so that surgery can be performed under endoscopic observation;
    transmitting said control to be given to said surgical instrument and/or said patient information as well as endoscopic images produced in said operating room to a remote place via said control means over a communication line; and
    displaying said control to be given to said surgical instrument in said operating room and/or said patient information as well as said endoscopic images on a monitor in the remote place.

11. A surgical information display method according to claim 10, further comprising:
    a step of transmitting support information useful in surgery from said remote place to said operating room over a communication line, and
    a step of displaying the support information.

12. A remote surgery support system by which a surgical procedure performed by a first person at an operating facility at a first location may be supported by a second person at a support facility at a remote second location, the system comprising:

a first input device located at the operating facility to input control commands for controlling a surgical instrument used by the first person at the operating facility;

a first control device at the operating facility for controlling the state of the surgical instrument based on the control commands inputted by the first input device;

a first signal processing device at the operating facility connectable to a communication channel between the operating facility and the support facility and operative to receive a signal from the first control device corresponding to the state of the surgical instrument and to convert the received signal into a signal which can be transmitted over the communication channel;

a second signal processing device connectable to the communication channel at the support facility, and responsive to a signal received over the communication channel to generate a signal corresponding to the controlled state of a surgical instrument at the operating facility, a second control device at the support facility connected to the second signal processing device; and a first display device at the support facility connected to the second control device for use by the second person, the second control device being responsive to an output of the second signal processing device to display information representative of the controlled state of the surgical instrument on the first display device.

13. A remote surgery support system according to claim 12, wherein said communication line is an integrated services digital network (ISDN), a LAN, or a WAN.

14. A remote surgery support system according to claim 12, further comprising:

a second input device located at the support facility, and usable to generate support information for transmission to the operating facility;

the second control device being responsive to the second input device to generate a support signal;

the second signal processing device being operative to transmit a signal corresponding to the support signal over the communication channel to the operating facility; and a second display device located at the operating facility, the first signal processing device being responsive to a signal received from the support facility to display the support information generated at the support facility on the second display device.

15. A remote surgery support system according to claim 14, further comprising:

an endoscopic imaging device located in the operating room and controlled by said first control device to provide an image of an intracavitary region of a patient;

the endoscopic imaging device being coupled to the first signal processing device whereby a video signal representing the intracavitary region is transmitted to the second signal processing device over the communication channel.

16. A remote surgery support system according to claim 15, further comprising a signal isolating device for electrically isolating the endoscopic imaging device and the first control device from the first signal processing device.

17. A remote surgery support system according to claim 15, wherein the video signal transmitted to said second signal processing device is displayed on a third display device.

18. A remote surgery support system according to claim 15, wherein the video signal transmitted to said second signal processing device is displayed on a display device controlled by the second control device.

19. A remote surgery support system according to claim 18, wherein said second control device includes a still image capturing device for capturing a still image from the video signal.

20. A remote surgery support system according to claim 19, wherein the support information generated by the second control device is comprised of a superposition of information generated using the second input device and the captured still image.

21. A remote surgery support system, comprising:

a first control device for controlling a surgical instrument used to perform surgery on a patient in an operating room;

a first input device coupled to the first control device by which a user in the operating room can input control information for the surgical instrument, and/or information concerning the patient;

a communication channel connecting the operating room to a control room at a remote location;

a first signal processing device connected to the first control device, and operative to generate signals representative of the control information and/or the patient information for transmission over the communication channel to the control room;

a second signal processing device connected to the communication channel in the control room, and operative to receive signals generated by the first signal processing device, and to convert the received signals into signals corresponding to the control information and/or the patient information that have not been converted by the first signal processing device;

a second control device responsive to output signals from the second signal processing device; and a first display device for displaying an output of said second control device, the first display device being accessible to a support person in the control room whereby the support person may observe the control information and/or the patient information.

* * * * *